"(12) United States Patent" Mori et al.

(10) Patent No.: US 6,646,104 B1
(45) Date of Patent: Nov. 11, 2003

(54) PROCESS FOR PRODUCTION OF SULFUR COMPOUNDS

(75) Inventors: Katsuhiro Mori, Tokuyama (JP); Tadashi Hara, Tokuyama (JP); Junji Momoda, Tokuyama (JP)

(73) Assignee: Tokuyama Corporation, Yamaguchi-ken (JP)

( * ) Notice: Subject to any disclaimer, the term of this patent is extended or adjusted under 35 U.S.C. 154(b) by 53 days.

(21) Appl. No.: 09/890,232

(22) PCT Filed: Dec. 1, 2000

(86) PCT No.: PCT/JP00/08522

§ 371 (c)(1),
(2), (4) Date: Jul. 30, 2001

(87) PCT Pub. No.: WO01/40175

PCT Pub. Date: Jun. 7, 2001

(30) Foreign Application Priority Data

Dec. 2, 1999 (JP) .............................. 11-343779
Feb. 29, 2000 (JP) ........................ 2000-053276
Oct. 12, 2000 (JP) ........................ 2000-312535

(51) Int. Cl.$^7$ ....................... C08G 75/00; C08F 228/00; C08F 228/06
(52) U.S. Cl. .................... 528/377; 528/373; 525/328.5; 525/535
(58) Field of Search ................ 528/377, 373; 525/328.5, 535

(56) References Cited

FOREIGN PATENT DOCUMENTS

JP   5-194486   *   8/1993
JP   8-41049    *   2/1996

OTHER PUBLICATIONS

Tsuyoshi et al. Preparation, characterization, and optical properties od disulfide—[S–alkylcarbamate], 1999, Chem Abstract 130:325449.*
Tsuyoshi et al. Synthesis, characterization, and optical properties of polymer comprising 1,4–dithiane–2,5–bis(thiomethyl) group, 1998, Chem Abstract 129: 16592.*
Fumie, 1,4–Dithiane ring containing vinyl compounds and isomeric mixtures thereof, 1996, Chem Abstract 124; 345012.*

* cited by examiner

Primary Examiner—Duc Truong
(74) Attorney, Agent, or Firm—Sherman & Shalloway

(57) ABSTRACT

A method of preparing a sulfur-containing compound having at least one thio group in the molecules by reacting a thiol compound with an organic compound having at least one functional group capable of forming a thio group in the molecules upon reacting with a mercapto group in the presence of a basic compound, wherein the number of moles of water contained in the reaction system is set to be not larger than 7.5 times as large as the number of moles obtained by multiplying the number of moles of the thiol compound to be reacted by a number of mercapto groups present in one molecule of the thiol compound.

7 Claims, No Drawings

PROCESS FOR PRODUCTION OF SULFUR COMPOUNDS

TECHNICAL FIELD

The present invention relates to a method of preparing a sulfur-containing compound having at least one thio group in the molecules by reacting a thiol compound with an organic compound having at least one functional group capable of forming a thio group in the molecules upon the reaction with a mercapto group, easily, in a high yield and in a highly pure form being colored little. The invention further relates to a sulfur-containing compound of a highly pure form obtained by the above method.

It is expected that the sulfur-containing compound having a thio group in the molecules can be used as an optical material that exhibits a high refractive index owing to its relatively large molecular refraction possessed by a sulfur atom and can be used in the field of medicines and agricultural chemicals owing to a high degree of activity exhibited by sulfur for animals and plants. In particular, the sulfur-containing compound is very useful as a polymerizable monomer or an intermediate product thereof for obtaining an optical material in a field where a high degree of refractive index is desired as represented by photochromic plastic lenses.

BACKGROUND ART

In the field of plastic lenses in recent years, attention has been given to those highly functional materials to which photochromic properties are imparted. Photochromic property is a reversible action of a material which quickly changes its color when irradiated with light containing ultraviolet rays such as of sunlight or light of a mercury lamp, and exhibits its initial color when the material is no longer irradiated with light but is placed in a dark place. A photochromic plastic lens is obtained by dispersing a photochromic compound having the above-mentioned property in a plastic lens. As the polymerization-curable compositions for obtaining the photochromic plastic lenses, there have been known photochromic curable compositions obtained by dissolving a photochromic compound in a radically polymerizable monomer as disclosed in Japanese Unexamined Patent Publication (Kokai) No. 124790/1991 and PCT International Patent Application No. 96/19741.

It has further been demanded to produce plastic lenses having smaller thicknesses. For example, the cured products obtained by curing the above-mentioned photochromic curable composition exhibit refractive indexes of smaller than 1.55, and it has been desired to further increase the refractive index from the standpoint of producing stronger lenses yet having smaller thicknesses.

It has generally known that a resin that exhibits a high refractive index can be realized by introducing halogen atoms other than fluorine, or by introducing aromatic rings or sulfur atoms in large amounts into the molecules of the polymerizable monomer. Among these methods, the method of introducing sulfur atoms into the monomer molecules is particularly effective from such a standpoint that the weight of the polymer (i.e., plastic lens) does not increase compared to the case of introducing halogen atoms other than fluorine or introducing aromatic rings and, besides, Abbe's number does not decrease.

When sulfur atoms are introduced into the molecules of the polymerizable compound, however, offensive odor is in many cases produced in working the finally obtained polymer (plastic lens). Besides, sulfur atoms must be introduced in large amounts from the standpoint of increasing the refractive index. Because of these reasons, there has not yet been obtained a highly refractive photochromic plastic lens which is satisfactory to a sufficient degree by using sulfur-containing polymerizable monomers.

As described above, no photochromic plastic lens has ever been known which is highly refractive, light in weight and exhibiting a large Abbe's number. It has therefore been desired to develop a method of preparing a polymerizable monomer for forming such a photochromic plastic lens maintaining a high yield and a high purity.

The present inventors have studied the method of introducing thio groups into the molecules of a polymerizable monomer based on such an idea that sulfur atoms can be introduced in large amounts into the monomer molecules by introducing sulfur atoms in the form of thio groups and that the refractive index of a polymer can be increased due to this effect.

Concerning the method of introducing thio groups into the molecules, Journal of American Chemical Society, 74, 828, 1952 teaches that an ethylphenylthio ether is obtained maintaining an yield of 82% by reacting a thiophenol with an ethyl bromide in the presence of sodium. The present inventors have attempted to synthesize a polymerizable sulfur-containing compound having thio groups relying on the sulfide-forming reaction by removing hydrogen halide by using an organohalide and metal sodium in compliance with the above-mentioned method only, however, to find that the reaction yield was from 70 to 80% involving much problem if the method is to be put into practice on an industrial scale.

According to the above method, further, use of metal sodium makes the operation cumbersome. In order to improve operability, therefore, the reaction was conducted by using an aqueous solution of sodium hydroxide instead of sodium. As a result, though the operability was improved, by-products were formed due to side reactions and, hence, the purity was low and, besides, color was observed.

Further, the polymerizable sulfur-containing compound obtained by the above method was evaluated for its performance as a monomer for producing photochromic plastic lenses. As a result, though the refractive index could be increased, there occurred a new problem in that the light resistance of photochromic properties was markedly deteriorated.

DISCLOSURE OF THE INVENTION

It is therefore an object of the present invention to provide a method of preparing a sulfur-containing compound having a thio group in the molecules by reacting a thiol compound with an organic halogen compound in the presence of a basic compound such as sodium hydroxide, the method requiring easy operation, featuring a high reaction yield of the object compound and free from the problem of coloring caused by impurities.

The invention further has an object of providing a method of preparing the sulfur-containing compound, wherein when the sulfur-containing compound having a polymerizable functional group is used as a monomer for forming the photochromic plastic lens, photochromic property having good light resistance is exhibited.

The present invention was proposed in order to solve the above-mentioned objects and was completed based on a discovery that a sulfur-containing compound which is an object compound is obtained suppressing the formation of impurities, suppressing the development of color in the product, maintaining a high purity and a high yield by controlling the amount of water in the reaction system to be smaller than a predetermined value, and that, in addition to the above, when the above reaction is conducted in an atmosphere without substantially containing oxygen such as nitrogen atmosphere, formation of the disulfide compounds, which are the impurities, is suppressed to a high degree, the disulfide compounds exhibiting chemical and physical behaviors resembling to those of the object sulfur-containing compound and, as a result, light resistance of the photochromic property is markedly improved when the above sulfur-containing compound is used as the monomer for forming photochromic plastic lenses.

That is, the present invention is concerned with a method of preparing a sulfur-containing compound having at least one thio group in the molecules by reacting a thiol compound with an organic compound having at least one functional group capable of forming a thio group in the molecules upon reacting with a mercapto group in the presence of a basic compound, wherein the number of moles of water contained in the reaction system is set to be not larger than 7.5 times as large as the number of moles obtained by multiplying the number of moles of the thiol compound to be reacted by a number of mercapto groups present in one molecule of the thiol compound.

Another invention is concerned with a method of preparing a sulfur-containing compound wherein the method of preparing the sulfur-containing compound is carried out in an atmosphere without substantially containing oxygen.

A further invention is concerned with a sulfur-containing compound of a highly pure form, which is a reaction product obtained by reacting a thiol compound with an organic compound having at least one functional group capable of forming a thio group in the molecules upon the reaction with a mercapto group or is a derivative of said reaction product and having at least one thio group in the molecules, said sulfur-containing compound containing not larger than 2 mol % of the compounds having a disulfide bond, which are the impurities.

A still further invention is concerned with a polymerizable monomer composition comprising the above sulfur-containing compound of a highly pure form and another polymerizable monomer copolymerizable therewith, wherein the content of the compound having a disulfide bond contained in said composition is not larger than 0.02 mols per mole of said sulfur-containing compound.

A yet further invention is concerned with a photochromic polymerization-curable composition containing the above polymerizable monomer composition and a photochromic compound.

A further invention is concerned with a photochromic cured product obtained by curing the photochromic polymerization-curable composition by polymerization.

BEST MODE FOR CARRYING OUT THE INVENTION

In the present invention, there is no particular limitation on the thiol compound which is a starting material for obtaining the sulfur-containing compound provided it has one or more mercapto groups in the molecules, and any known thiol compound can be used. As another starting material, i.e., the organic compound (capable of reacting with the mercapto group) having at least one functional group capable of forming a thio group (the thio group-forming functional group) in the molecules upon the reaction with the mercapto group, there can be used any known compound without particular limitation provided it is capable of forming a thio group (synonymous with a group —S— without, however, including those in which the thio groups are continuing like a group —S—S—) in the molecules upon the reaction with the mercapto group. Here, the functional group capable of forming a thio group upon the reaction with the mercapto group is the one capable of forming a bond having a thio group, such as sulfide bond, thioester bond, thiourethane bond or thiocarbonate bond upon the reaction with the mercapto group, as represented by halogen atoms as well as radically polymerizable, ionically polymerizable, polyadditive or polycondensing polymerizable functional group, such as (meth)acryloyl group, (meth)acryloyloxy group, hydroxyl group, mercapto group, isocyanate group, thioisocyanate group, vinyl group, styryl group, aryloxy group, epoxy group, epithio group, amino group and carboxyl group.

According to the present invention, the thiol compound is reacted with a compound capable of reacting with the mercapto group to prepare a sulfur-containing compound having at least one thio group in the molecules. In this case in the method of the present invention, there is used a basic compound such as sodium hydroxide that can be easily handled compared with metal sodium. In this case, further, the conversion is higher than that of when sodium metal is used and, besides, by-products are formed in small amounts.

Among the preparation methods of the present invention, it is desired to employ:

① a method of preparing a sulfur-containing compound having at least one thio group in the molecules represented by the following general formula (7) by reacting a thiol compound represented by the following general formula (1) with an organic compound represented by the following general formula (6) having at least one functional group capable of forming a thio group in the molecules upon the reaction with a mercapto group;

② a method of preparing a sulfur-containing compound having at least one thio group in the molecules represented by the following general formula (8) by reacting a thiol compound represented by the following general formula (2) with an organic compound represented by the following general formula (6) having at least one functional group capable of forming a thio group in the molecules upon the reaction with a mercapto group;

③ a method of preparing a sulfur-containing compound having at least one thio group in the molecules represented by the following general formula (9) by reacting a thiol compound represented by the following general formula (3) with an organic compound represented by the following general formula (6) having at least one functional group capable of forming a thio group in the molecules upon the reaction with a mercapto group;

④ a method of preparing a sulfur-containing compound having at least one thio group in the molecules represented by the following general formula (10) by reacting a thiol compound represented by the following general formula (4) with an organic compound represented by the following general formula (6) having at least one functional group capable of forming a thio group in the molecules upon the reaction with a mercapto group; or ⑤ a method of preparing a sulfur-containing compound having at least one thio group in the molecules represented by the following general formula (11) by reacting a thiol compound represented by the following general formula (5) with an organic compound represented by the following general formula (6) having at least one functional group capable of forming a thio group in the molecules upon the reaction with a mercapto group;

from the standpoint of utility of the object product, such as when the sulfur-containing compound having a polymerizable functional group is used as a monomer for forming photochromic plastic lenses, the obtained photochromic plastic lenses exhibit good lens properties (mechanical properties such as hardness, refractive index, Abbe's number, etc.) and good photochromic properties (color density, color-developing/color-fading rate, light resistance, etc.).

That is, a thiol compounds such as:

a compound represented by the following general formula (1),

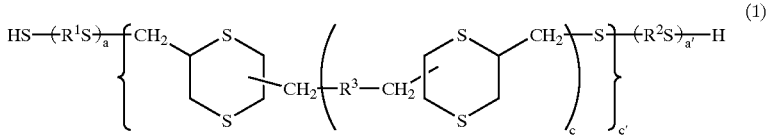

wherein $R^1$ and $R^2$ are, independently from each other, alkylene groups with 1 to 4 carbon atoms that may have a substituent (without, however, including the number of carbon atoms of the substituent) or arylene groups with 6 to 12 carbon atoms that may have a substituent (without, however, including the number of carbon atoms of the substituent), the substituent of each of said alkylene group and of said arylene group being an alkyl group, an aryl group, an aralkyl group, an alkoxy group, an alkylthio group, an aromatic heterocyclic group, a halogen atom excluding fluorine, or at least one group selected from the group consisting of groups represented by the following formula (12)

 (12)

wherein $R^4$ is an alkylene group with 1 to 4 carbon atoms that may have a substituent (without, however, including the number of carbon atoms of the substituent), the substituent of said alkylene group being at least one group selected from the group consisting of an alkyl group, an aryl group, an aralkyl group, an alkoxy group, an alkylthio group, an aromatic heterocyclic group and a halogen atom excluding fluorine, and d is an integer of from 0 to 10;

$R^3$ is a divalent group represented by the following formula (13),

 (13)

wherein $R^5$ is an alkylene group with 1 to 4 carbon atoms that may have a substituent (without, however, including the number of carbon atoms of the substituent), an arylene group with 6 to 12 carbon atoms that may have a substituent (without, however, including the number of carbon atoms of the substituent), a divalent aromatic heterocyclic group that may have a substituent, or a divalent group represented by the following formula (14),

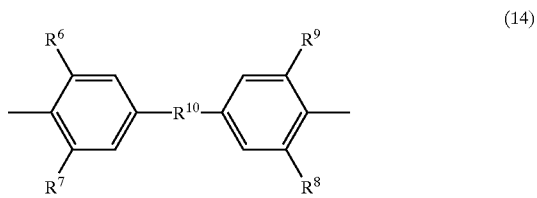

(wherein $R^6$, $R^7$, $R^8$ and $R^9$ are, independently from each other, halogen atoms excluding fluorine atoms, or hydrogen atoms, and $R^{10}$ is an alkylene group having 1 to 3 carbon atoms or sulfur atoms), the substituent of each of said alkylene group, arylene group and divalent aromatic heterocyclic group being the same as the substituent of the alkylene group with 1 to 4 carbon atoms that may have a substituent in the above formula (12), and e being an integer of 0 to 5; and a and a' are, independently from each other, integers of 0 to 10, c is an integer of from 0 to 6, c' is 0 or 1 and, when c' is 0, the sum of a and a' is not smaller than 2; or a compound represented by the following general formula (2),

 (2)

wherein $R^{15}$ is a monovalent to trivalent aromatic group with 6 to 14 carbon atoms which may have a substituent (without, however, including the number of carbon atoms of the substituent) or a monovalent to trivalent aromatic heterocyclic group with 3 to 12 carbon atoms which may have a substituent (without, however, including the number of carbon atoms of the substituent), the substituent of each of these aromatic group and aromatic heterocyclic group being the same as the substituent of the alkylene group with 1 to 4 carbon atoms which may have a substituent in the above formula (12), and f is, independently from each other, and f' is an integer of 1 to 3; or a compound represented by the following general formula (3),

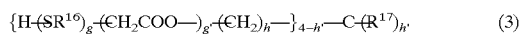

wherein $R^{16}$ is an alkylene group with 1 to 4 carbon atoms which may have a substituent (without, however, including the number of carbon atoms of the substituent), the substituent of said alkylene group being the same as the substituent of the alkylene group with 1 to 4 carbon atoms that may have a substituent denoted by $R^1$ and $R^2$ in the above general formula (1), $R^{17}$ is a hydrogen atom or an alkyl group with 1 to 4 carbon atoms which may have a substituent (without, however, including the number of carbon atoms of the substituent), the substituent of said alkyl group being the same as the substituent other than the alkyl group in the alkylene group with 1 to 4 carbon atoms that may have a substituent in the above formula (12), g' is an integer of 0 or 1, g is an integer of 1 to 10, h is an integer of 0 to 5 and, when g' is 1, h is an integer of 1 to 5, and h' is 0 or 1; or a compound represented by the following general formula (4),

wherein $R^{18}$ and $R^{19}$ are, independently from each other, alkylene groups with 1 to 4 carbon atoms that may have a substituent (without, however, including the number of carbon atoms of the substituent) or arylene groups with 6 to 12 carbon atoms that may have a substituent (without, however, including the number of carbon atoms of the substituent), the substituent of each of said alkylene group and said arylene group being the same as the substituent of the alkylene group with 1 to 4 carbon atoms which may have a substituent and of the arylene group with 6 to 12 carbon atoms which may have a substituent denoted by $R^1$ and $R^2$ in the above general formula (1), $R^{20}$ is an alkyl group with 1 to 4 carbon atoms which may have a substituent (without, however, including the number of carbon atoms of the substituent), an aryl group with 6 to 12 carbon atoms which may have a substituent (without, however, including the number of carbon atoms of the substituent), or an aralkyl group which may have a substituent, the substituent of said alkyl group being the same as the substituent other than the alkyl group in the alkylene group with 1 to 4 carbon atoms which may have a substituent in the above formula (12), the substituent of each of said aryl group and said aralkyl group being the same as the substituent of the alkylene group with 1 to 4 carbon atoms that may have a substituent in the above formula (12), Y is an oxygen atom or a sulfur atom, Z is an oxygen atom or a sulfur atom, it does no happen that both Y and Z are simultaneously oxygen atoms, i and i' are, independently from each other, integers of 0 to 10, and the sum of i and i' is not smaller than 1; or a compound represented by the following general formula (5),

wherein $R^{21}$, $R^{22}$, $R^{23}$, $R^{24}$, $R^{25}$ and $R^{26}$ are, independently from each other, hydrogen atoms or groups represented by the following formula (16),

wherein $R^{27}$ and $R^{28}$ are, independently from each other, alkylene groups with 1 to 4 carbon atoms that may have a substituent (without, however, including the number of carbon atoms of the substituent), the substituent of said alkylene group being the same as the substituent of the alkylene group with 1 to 4 carbon atoms which may have a substituent represented by $R^1$ and $R^2$ in the above general formula (1), j and j' are, independently from each other, integers of 0 to 4, and the sum of j and j' is not smaller than 1; and at least one of $R^{21}$, $R^{22}$, $R^{23}$, $R^{24}$, $R^{25}$ and $R^{26}$ is the group represented by the above formula (16);

is reacted with an organic compound having at least one functional group capable of forming a thio group in the molecules upon the reaction with a mercapto group, represented by the following general formula (6),

wherein W is a functional group capable of forming a thio group upon reacting with a mercapto group, and $R^{11}$ is an alkyl group with 1 to 4 carbon atoms that may have a substituent (without, however, including the number of carbon atoms of the substituent), or a (meth)acryloyl group, the substituent of said alkyl group being at least the one selected from the group consisting of a polymerizable functional group, an aryl group, an aralkyl group, an alkoxy group, an alkylthio group, an aromatic heterocyclic group and a halogen atom excluding fluorine;

to form a sulfur-containing compound having at least one thio group in the molecules, such as:

a compound represented by the following general formula (7),

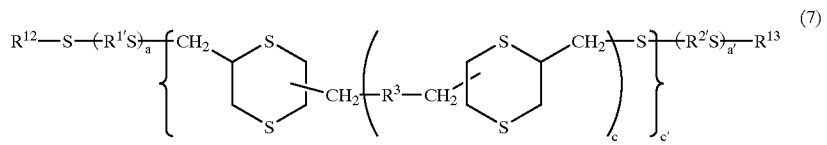

wherein $R^1$ and $R^2$ are, independently from each other, alkylene groups with 1 to 4 carbon atoms that may have a substituent (without, however, including the number of carbon atoms of the substituent) or arylene groups with 6 to 12 carbon atoms that may have a substituent (without, however, including the number of carbon atoms of the substituent), the substituent of each of said alkylene group and of said arylene group being at least the one selected from the group consisting of an alkyl group, an aryl group, an aralkyl group, an alkoxy group, an alkylthio group, an aromatic heterocyclic group, a halogen atom excluding fluorine, and a group represented by the following formula (15)

  (15)

wherein $R^4$ is as defined in the above formula (12), $R^{14}$ is the same as $R^{11}$ in the above formula (6), d is an integer of from 0 to 10, and d' is an integer of 0 or 1;

$R^{12}$ and $R^{13}$ are, independently from each other, the same groups as those of $R^{11}$ of the above general formula (6), $R^3$ is as defined in the above general formula (1), a and a' are, independently from each other, integers of 0 to 10, c is an integer of from 0 to 6, c' is 0 or 1 and, when c' is 0, the sum of a and a' is not smaller than 2; or a compound represented by the following general formula (8),

  (8)

wherein $R^{15}$, f and f' are as defined in the above general formula (2), and $R^{11}$, independently from each other, is as defined in the above general formula (6); or a compound represented by the following general formula (9),

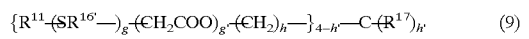  (9)

wherein $R^{16'}$ is an alkylene group with 1 to 4 carbon atoms that may have a substituent (without, however, including the number of carbon atoms of the substituent), the substituent of said alkylene group being the same as the substituent of the alkylene group with 1 to 4 carbon atoms which may have a substituent denoted by $R^{1'}$ and $R^{2'}$ in the above general formula (7), $R^{17}$, g, g', h and h' being as defined in the above general formula (3), and $R^{11}$ being, independently from each other the same as defined in the above formula (6); or a compound represented by the following general formula (10),

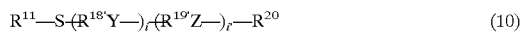  (10)

wherein $R^{18'}$ and $R^{19'}$ are, independently from each other, alkylene groups with 1 to 4 carbon atoms which may have a substituent (without, however, including the number of carbon atoms of the substituent), or arylene groups with 6 to 12 carbon atoms which may have a substituent (without, however, including the number of carbon atoms of the substituent), the substituent of each of said alkylene group and said arylene group being the same as the substituent of the alkylene group with 1 to 4 carbon atoms which may have a substituent or of the arylene group with 6 to 12 carbon atoms which may have a substituent denoted by $R^{1'}$ and $R^{2'}$ in the above general formula (7), and $R^{20}$, Y, Z, i and i' are as defined in the above general formula (4), and $R^{11}$ is as defined in the above general formula (6); or a compound represented by the following general formula (11),

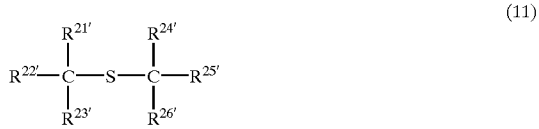  (11)

wherein $R^{21'}$, $R^{22'}$, $R^{23'}$, $R^{24'}$, $R^{25'}$ and $R^{26'}$ are, independently from each other, hydrogen atoms or groups represented by the following formula (17),

  (17)

wherein $R^{29}$ and $R^{30}$ are, independently from each other, alkylene groups with 1 to 4 carbon atoms that may have a substituent (without, however, including the number of carbon atoms of the substituent), the substituent of said alkylene group being the same as the substituent in the alkylene group with 1 to 4 carbon atoms which may have a substituent denoted by $R^{1'}$ and $R^{2'}$ in the above general formula (7), j and j' being as defined in the above formula (16), and $R^{11}$ being as defined in the above general formula (6); and at least one of $R^{21'}$, $R^{22'}$, $R^{23'}$, $R^{24'}$, $R^{25'}$ and $R^{26'}$ is a group represented by the above general formula (5).

Among the above-mentioned preparation methods ① to ⑤, the preparation method ① is desirable from such a standpoint that the obtained sulfur-containing compound is useful as a monomer for obtaining optical lenses having a high refractive index and a large Abbe's number or as an intermediate monomer product for obtaining such optical lenses. From such a standpoint that the sulfur-containing compound is useful as an intermediate monomer product for obtaining optical lenses, further, it is particularly desired to use an organic compound having at least one functional group capable of forming a thio group in the molecules upon reacting with a mercapto group represented by the general formula (6) in which $R^{11}$ is an alkyl group with 1 to 4 carbon atoms having a reactive substituent such as a hydroxyl group, a mercapto group or a halogen atom.

According to the method of preparing the sulfur-containing compound of the present invention, a thiol compound is reacted with an organic compound having at least one functional group capable of forming a thio group in the molecules upon the reaction with a mercapto group in the presence of a basic compound in order to substitute an organic group for a hydrogen atom of the mercapto group (group -SH) in the thiol compound, thereby to obtain, as an object product, a sulfur-containing compound having a chain extended due to an organic residue substituted by newly forming a thio group. According to the preparation method of the present invention, therefore, there is prepared a sulfur-containing compound having at least one thio group in the molecules. It is generally desired to prepare, as an object product, a sulfur-containing compound having not less than two thio groups in the molecules by using, as the thiol compound, a compound having one or more thio groups in the molecules.

The thiol compound used as a starting material in the preparation method of the present invention may be any known compound without limitation provided it has one or more mercapto groups in the molecules. From the standpoint of usefulness of the formed product, however, it is desired to use a thiol compound represented by the above general formula (1), (2), (3), (4) or (5). These thiol compounds will now be described.

The thiol compound represented by the above general formula (1) will be described, first.

In the above general formula (1), $R^1$ and $R^2$ are, independently from each other, alkylene groups with 1 to 4 carbon atoms which may have a substituent or arylene groups with 6 to 12 carbon atoms which may have a substituent. Here, however, the number of carbon atoms does not include those carbon atoms of the substituent.

Among the alkylene groups with 1 to 4 carbon atoms, those without substituent are, concretely, ethylene group, propylene group, isopropylene group and butylene group. Among them, ethylene group is particularly preferred. Among the arylene groups with 6 to 12 carbon atoms, further, those without substituent are, concretely, phenylene group, tolylene group, xylylene group and naphthylene group.

The substituent possessed by the alkylene group or the arylene group is at least the one selected from the group consisting of alkyl group, aryl group, aralkyl group, alkoxy group, alkylthio group, aromatic heterocyclic group, halogen atom excluding fluorine and group represented by the above general formula (12). These substituents will now be described.

As the alkyl group which is the substituent, any known group can be used without limitation. It is, however, desired to use an alkyl group with 1 to 4 carbon atoms, such as methyl group, ethyl group, propyl group, isopropyl group, butyl group or t-butyl group.

As the aryl group which is the substituent, any known group can be used without limitation. It is, however, desired to use an aryl group with 6 to 12 carbon atoms, such as phenyl group, tolyl group or naphthyl group.

As the aralkyl group which is the substituent, any known group can be used without limitation. It is, however, desired to use an aralkyl group with 7 to 11 carbon atoms, such as benzyl group or phenetyl group.

As the alkoxy group which is the substituent, any known group can be used without limitation. It is, however, desired to use an alkoxy group with 1 to 4 carbon atoms, such as methoxy group, ethoxy group, propoxy group, isopropoxy group, butoxy group or t-butoxy group.

As the alkylthio group which is the substituent, any known group can be used without limitation. It is, however, desired to use an alkylthio group with 1 to 4 carbon atoms, such as methylthio group, ethylthio group, propylthio group, isopropylthio group, butylthio group or t-butylthio group.

As the aromatic heterocyclic group which is the substituent, any known group can be used without limitation. It is, however, desired to use an aromatic heterocyclic group with 4 to 10 carbon atoms, such as thienyl group, furyl group or benzothienyl group.

As the halogen atom excluding fluorine as the substituent, there can be used chlorine, bromine or iodine.

In the substituent in the above formula (12), $R^4$ is an alkylene group with 1 to 4 carbon atoms which may have a substituent. Here, however, the number of carbon atoms does not include carbon atoms of the substituent. Among the alkylene groups with 1 to 4 carbon atoms, those without substituent are, concretely, methylene group, ethylene group, propylene group, isopropylene group and butylene group. Among them, ethylene group is particularly preferred.

The substituent of the alkylene group which may have a substituent denoted by $R^4$ is at least the one selected from the group consisting of alkyl group, aryl group, aralkyl group, alkoxy group, alkylthio group, aromatic heterocyclic group and halogen atom excluding fluorine. The substituent may be the same as that of the alkylene group that may have a substituent or may be the same as that of the arylene group that may have a substituent denoted by $R^1$ and $R^2$. It is, however, desired to use ethylene group, isopropylene group or phenylene group. Among them, it is particularly desired to use ethylene group or isopropylene group.

In the above formula (12), further, d is an integer of 0 to 10. From the standpoint of easy synthesis, however, it is desired that d is an integer of 0 to 3.

There is no particular limitation on the number of the substituents. When the number of the substituents is not smaller than 2, different substituents may be substituted for.

In the above general formula (1), $R^3$ is a group represented by the above formula (13).

In the above formula (13), e is an integer of 0 to 5 and, preferably, an integer of 0 to 4.

In the above formula (13), further, $R^5$ is an alkylene group with 1 to 4 carbon atoms which may have a substituent (without, however, including the number of carbon atoms of the substituent), an arylene group with 6 to 12 carbon atoms which may have a substituent (without, however, including the number of carbon atoms of the substituent), a divalent aromatic heterocyclic group which may have a substituent, or a group represented by the above general formula (14).

In the above formula (14), $R^6$, $R^7$, $R^8$ and $R^9$ are, independently from each other, halogen atoms excluding fluorine atoms, or hydrogen atoms, and $R^{10}$ is an alkylene group with 1 to 3 carbon atoms or a sulfur atom. Concretely, the alkylene group is a methylene group, an ethylene group or a propylene group. It is, however, desired that $R^{10}$ is a sulfur atom from the standpoint of easy availability of the starting material.

The alkylene group and arylene group denoted by $R^5$ may be the same as those denoted by $R^1$ and $R^2$, and are, desirably, ethylene groups, isopropylene groups or phenylene groups and, particularly preferably, ethylene groups or isopropylene groups. The substituents thereof are the same as those of the alkylene group that may have a substituent denoted by $R^4$.

As the aromatic heterocyclic group that may have a substituent denoted by $R^5$, further, any known group can be used without limitation. It is, however, desired to use an aromatic heterocyclic group with 4 to 10 carbon atoms, such as thienyl group, furyl group or benzothienyl group, or a group thereof for which are substituted one or two or more substituents of the alkylene group that may have a substituent denoted by $R^4$.

In the above general formula (1), c is an integer of 0 to 6. From the standpoint of easy availability of the starting material or easy synthesis, however, it is desired that c is an integer of 0 to 3. In the above general formula (1), the positions where the group —$CH_2$— (when c is 0) and the group —$CH_2$—$R_3$—$CH_2$— (when c is not 0) are bonded to the dithian ring may be such that the dithian rings become a 2,5-substituted 1,4-dithian ring or a 2,6-substituted 1,4-dithian ring. When c is not smaller than 1, positions may be such that they are arbitrarily mixed together.

In the above general formula (1), c' is 0 or 1. From the standpoint of easy synthesis, however, it is desired that c' is 0. As an intermediate product of the optical material, on the other hand, it is desired that c' is 1.

In the above general formula (1), a and a' are, independently from each other, integers of 0 to 10. From the standpoint of easy availability of the starting material or easy synthesis, however, it is desired that a and a' are integers of 0 to 6. When c' is 0 in the above general formula (1), the sum of a and a' is not smaller than 2.

Next, described below is the compound represented by the above general formula (2).

In the above general formula (2), $R^{15}$ is a monovalent to trivalent aromatic group with 6 to 14 carbon atoms which may have a substituent (without, however, including the number of carbon atoms of the substituent) or a monovalent to trivalent aromatic heterocyclic group with 3 to 12 carbon atoms which may have a substituent (without, however, including the number of carbon atoms of the substituent). The substituents of these groups are the same as the substituent of the alkylene group with 1 to 4 carbon atoms which may have a substituent of the above formula (12). Concrete examples of the monovalent to trivalent aromatic group or of the monovalent to trivalent aromatic heterocyclic group include phenylene group, tolylene group, xylylene group, naphthylene group, thienyl group, furyl group, benzothienyl group and triazine group. Among them, it is particularly desired to use phenylene group from the standpoint of easy availability of the starting material.

In the above general formula (2), f is, independently from each other, an integer of 0 or 1. From the standpoint of easy synthesis and easy availability of the starting material, it is desired that f' is 1. From the standpoint of monomer for photochromic lenses having a high refractive index, it is desired that f' is 3.

Next, described below is the compound represented by he above general formula (3).

In the above general formula (3), $R^{16}$ is an alkylene group with 1 to 4 carbon atoms which may have a substituent. Here, however, the number of carbon atoms does not include the number of carbon atoms of the substituent. The alkylene group with 1 to 4 carbon atoms that may have a substituent may be the same as the alkylene group with 1 to 4 carbon atoms which may have a substituent denoted by $R^1$ and $R^2$.

In the above general formula (3), $R^{17}$ is a hydrogen atom or an alkyl group with 1 to 4 carbon atoms which may have a substituent. Here, however, the number of carbon atoms does not include the carbon atoms of the substituent. The substituent possessed by the alkyl group may be the same as the substituent, other than the alkyl group, in the alkylene group with 1 to 4 carbon atoms which may have a substituent in the above formula (12). Concrete examples of the alkyl group include methyl group, ethyl group, propyl group, isopropyl group and butyl group. Among them, it is particularly desired to use methyl group.

In the above general formula (3), g is an integer of 1 to 10. From the standpoint of easy availability of the starting material and easy synthesis, however, g is preferably an integer of 1 to 5. In the general formula (3), further, g' is an integer of 0 to 1. In the same formula, h is an integer of 0 to 5. From the standpoint of easy availability and easy synthesis, however, h is 1 to 3. In the same formula, further, h' is 0 or 1. From the standpoint of easy synthesis, however, h' is 1.

Next, described below is the compound represented by the above general formula (4).

In the above general formula (4), $R^{18}$ and $R^{19}$ are, independently from each other, alkylene groups with 1 to 4 carbon atoms which may have a substituent (without, however, including the number of carbon atoms of the substituent) or arylene groups with 6 to 12 carbon atoms which may have a substituent (without, however, including the number of carbon atoms of the substituent). The alkylene groups with 1 to 4 carbon atoms that may have a substituent and the arylene groups that may have a substituent denoted by $R^{18}$ and $R^{19}$ may be the same as those denoted by $R^1$ and $R^2$, and, preferably, ethylene groups, isopropylene groups or phenylene groups and, particularly preferably, ethylene groups or isopropylene groups.

In the above general formula (4), $R^{20}$ is an alkyl groups with 1 to 4 carbon atoms which may have a substituent, an aryl group with 6 to 12 carbon atoms which may have a substituent or an aralkyl group which may have a substituent. Here, however, the number of carbon atoms does not include the carbon atoms of the substituent. The alkyl group with 1 to 4 carbon atoms which may have the substituent may be the same as the alkyl group with 1 to 4 carbon atoms denoted by $R^{17}$. Further, the substituents possessed by the aryl group and aralkyl group are the same as the substituent of the alkylene group with 1 to 4 carbon atoms which may have a substituent in the above formula (12).

In the above general formula (4), Y and Z are oxygen atoms or sulfur atoms. Here, however, Y and Z are not oxygen atoms at the same time. As the monomer for obtaining photochromic plastic lenses having a high refractive index, it is desired that Y and Z are both sulfur atoms.

In the above general formula (4), i and i' are, independently from each other, integers of 0 to 10, and the sum of i and i' is not smaller than 1.

Finally, described below is the compound represented by the above general formula (5).

In the above general formula (5), $R^{21}$, $R^{22}$, $R^{23}$, $R^{24}$, $R^{25}$ and $R^{26}$ are, independently from each other, hydrogen atoms or groups represented by the above formula (16). Here, however, at least one of $R^{21}$, $R^{22}$, $R^{23}$, $R^{24}$, $R^{25}$ and $R^{26}$ in the above general formula (5) is the group represented by the above formula (16).

In the above formula (16), $R^{27}$ and $R^{28}$ are, independently from each other, alkylene groups with 1 to 4 carbon atoms which may have a substituent. Here, however, the number of carbon atoms does not include the carbon atoms of the substituent. The substituents of the alkylene groups are the same as the substituent of the alkylene group with 1 to 4 carbon atoms which may have a substituent denoted by $R^1$ and $R^2$ in the above general formula (1).

In the above formula (16), further, j and j' are, independently from each other, integers of 0 to 4, and the sum of j and j' is not smaller than 1.

In the preparation method of the present invention, another starting material, i.e., an organic compound (capable of reacting with a mercapto group) having at least one functional group capable of forming a thio group (the thio group-forming functional group) in the molecules upon the reaction with a mercapto group, may be any known compound without limitation.

The reaction with the mercapto group for forming the thio group may be a reaction in which a hydrogen atom of the mercapto group is condensed while being split in the form of hydrogen halide or a reaction in which a sulfur atom and a hydrogen atom of the mercapto group are added while being split off to the unsaturated bond in the thio group-forming functional group. The combination of the thiol compound and the compound capable of reacting with the mercapto group may be suitably determined depending upon the kind of the reaction.

There is no particular limitation on the compound capable of reacting with the mercapto group provided it is an organic compound having a thio group-forming functional group in the molecules, and there can be used any one of a structure corresponding to the object compound and to the thiol compound that is used. The thio group-forming functional group is as described already. From the standpoint of easy availability of the starting material and easy synthesis, however, it is desired to use a halogen atom and, particularly, a chlorine atom, a bromine atom or an iodine atom when the thio group is to formed as a sulfide bond. When the thio group is to be formed as a thio ester bond, it is desired to use a halogen atom and, particularly, a chlorine atom. When the thio group is to be formed as a thiourethane bond, it is desired to use an isocyanate group or a thioisocyanate group. When the thio group is to be formed as a thiocarbonate bond, it is desired to use a carbonic acid ester.

When it is attempted to prepare a polymerizable monomer that is useful as an optical material such as of photochromic plastic lenses according to the method of the present invention, it is desired to use the thio group-forming functional group as well as a compound having at lest one polymerizable functional group as a compound capable of reacting with the mercapto group. Namely, it is desired to obtain the sulfur-containing compound of the present invention by forming a thio group while leaving the polymerizable functional group in the compound capable of reacting with the mercapto group. As the polymerizable functional group, there can be exemplified a variety of radically polymerizable, ionically polymerizable, polymerization additive or polymerization condensing functional group exemplified already as the thio group-forming functional group.

In preparing the polymerizable monomer, the thio group-forming functional group and the polymerizable functional group may be those of the same kind. However, the sulfur-containing compound which is the object product must have one thio group and one polymerizable functional group. Accordingly, the number of the groups must not be smaller than 2. In this case, further, the reaction is conducted by using the compound capable of reacting with the mercapto group and having in the molecules the number of the functional groups larger than the number of the mercapto groups present in the molecules of the thiol compound, so that the polymerizable groups are left in the reaction product (object product). When the thio group-forming functional group and the polymerizable functional group are of different kinds, the total number of the functional groups present in a molecule of the compound capable of reacting with the mercapto group may be selected to be larger than the number of the mercapto groups present in a molecule of the thiol compound in the same manner as described above to leave the polymerizable functional groups. In general, however, these two functional groups exhibit different reactivity to the mercapto group. Upon suitably setting the reaction conditions, therefore, the group having a low reactivity can be left as the polymerizable group. It is, hence, desired that the thio group-forming functional group and the polymerizable functional group are of different kinds.

The compound capable of reacting with the mercapto group used in the present invention is, usually, a compound represented by the above general formula (6).

In the above general formula (6), W is a thio group-forming functional group. In the above general formula (6), further, $R^{11}$ is an alkyl group with 1 to 4 carbon atoms which may have a substituent (without, however, including the number of carbon atoms of the substituent) or a (meth) acryloyl group. The substituent of the alkyl group is at least one group selected from the group consisting of polymerizable functional group, aryl group, aralkyl group, alkoxy group, alkylthio group, aromatic heterocyclic group and halogen atom excluding fluorine. As described already, from the standpoint of effectively using the compound of the above general formula (6) as a monomer or an intermediate product thereof for producing plastic lenses, it is desired that $R^{11}$ in the general formula (6) is an alkyl group with 1 to 4 carbon atoms having a polymerizable functional group as a substituent or a (meth)acryloyl group, or is, particularly, an alkyl group with 1 to 4 carbon atoms having a reactive substituent such as hydroxyl group, mercapto group or halogen atom which enables the polymerizable groups to be easily introduced.

There is no particular limitation on the amount of the compound capable of reacting with the mercapto group, that is used in the present invention. It is, however, desired to use the compound capable of reacting with the mercapto group in a number of moles which is 0.5 to 5.0 times as great and, particularly, which is 1.0 to 3.0 times as great as the number of moles obtained by multiplying the number of moles of the thiol compound that is to be reacted by the number of mercapto groups present in a molecule of the thiol compound.

In the present invention, the above-mentioned thiol compound is reacted with the compound capable of reacting with the mercapto group in the presence of a basic compound while controlling the amount of water in the reaction system to be not larger than 7.5 times as large as the number of moles obtained by multiplying the number of moles of the thiol compound by the number of mercapto groups present in a molecule of the thiol compound. upon controlling the amount of water by using the basic compound, it is allowed to obtain the desired product maintaining good operability and in a high yield. It is further allowed to favorably prevent the reaction product from being colored.

There is no particular limitation on the basic compound that is used provided it activates the mercapto group of the thiol compound and improves the reactivity with the compound capable of reacting with the mercapto group. From the standpoint of easy handling, however, it is desired to use a hydroxide of an alkali metal, a carbonate of an alkali metal, an alkoxide of an alkali metal or an organic base. Concrete examples of the basic compound that can be favorably used include lithium hydroxide, sodium hydroxide, potassium hydroxide, cesium hydroxide, lithium carbonate, sodium carbonate, potassium carbonate, cesium carbonate, sodium hydrogen carbonate, potassium hydrogen carbonate, lithium methoxide, sodium methoxide, sodium ethoxide, t-butoxypotassium, triethylamine, pyridine and quinoline. Among them, it is particularly desired to use a basic compound such as sodium hydroxide, potassium hydroxide, sodium carbonate, potassium carbonate, cesium carbonate, sodium methoxide, sodium ethoxide, t-butoxypotassium, triethylamine or pyridine from the standpoint of easy handling and solubility in an organic solvent (particularly in an alcohol). It is further allowable to use basic compounds of different kinds in a mixed manner.

There is no particular limitation on the amount of the basic compound. From the standpoint of trapping by-products such as hydrogen halide and the like and of preventing excess use, however, it is desired that the basic compound is used in a number of moles which is 0.5 to 5.0 times as large and, particularly, 1.0 to 3.0 times as large as the number of moles obtained by multiplying the number of mols of the thiol compound by the number of the mercapto groups in a molecule of the thiol compound.

In the preparation method of the present invention, the basic compound dissolves sparingly depending upon the kind of the reaction reagent that is used or depending upon the reaction solvent that is used as required. In order to enhance the solubility, therefore, water may be added, as required, to the reaction system. In conducting the reaction, however, it is essential to decrease the amount of water contained in the reaction system to be smaller than the above-mentioned particular value.

That is, the number of moles of water contained in the reaction system must be decreased to be not larger than 7.5 times as large as the number of moles (hereinafter also referred to as the number of moles of the starting mercapto groups) obtained by multiplying the number of moles of the thiol compound used as the starting material by the number of the mercapto groups present in a molecule of the thiol compound. When the amount of water contained in the reaction system exceeds the above amount, it is not possible to suppress the formation of by-products, whereby the reaction yield decreases and the formed product is colored. From the standpoint of suppressing the formation of by-products, it is desired that the amount of water in the reaction system is not larger than 5.0 times and, particularly, not larger than 2.5 times as large as the number of moles of the starting mercapto groups.

When use is made, as the basic compound, of a starting material used for the reaction or a water-soluble compound which is not almost soluble in an organic solvent that is used as required, it is desired to add water in an amount of not larger than 7.5 times and, particularly, not larger than 2.5 times as large as the number of moles of the starting mercapto groups from the standpoint of improving the solubility.

The amount of water in the reaction system can be limited by using the (dehydrated) reaction reagent or a dehydrated solvent, or by adding a basic compound that forms no water in the reaction with the mercapto group.

The amount of the water may be measured by measuring, in advance and relying upon Karl Fischer's method, the amount of water contained in the reaction reagent or in the solvent of before being mixed. Upon measuring the final amount of water contained in the reaction system after the reaction, further, it becomes possible to confirm the amount of water formed by the reaction relying upon the difference from a value of before the mixing.

In the present invention, it is particularly desired to conduct the reaction of the thiol compound with the compound capable of reacting with the mercapto group in an atmosphere without substantially containing oxygen while controlling the amount of the water.

That is, even when the above reaction is effected by simply controlling the amount of water, the object sulfur-containing compound can be obtained in a considerably high yield suppressing the formation of the by-product. Among the sulfur-containing compounds obtained by this method, however, when the one having a polymerizable functional group (hereinafter also referred to as polymerizable sulfur-containing compound) is evaluated for its performance as a monomer for obtaining photochromic plastic lenses, the object of high refractive index is accomplished but light resistance of photochromic properties is very deteriorated.

In order to solve this problem, the present inventors have closely analyzed the polymerizable sulfur-containing compound to investigate the cause of drop in the light resistance of photochromic properties. That is, the polymerizable sulfur-containing compound used for the evaluation is the one of which the purity is confirmed by gas chromatography (GC method) after the color has been removed by the treatment with activated carbon and by washing with an aqueous solution of sodium hydroxide, which, however, has not been carefully analyzed by the high-speed liquid chromatography (HPLC method). As a result, the polymerizable sulfur-containing compound could not be detected by the analysis based on the GC method. It was, however, learned that a compound (hereinafter also referred to as disulfide compound) having a disulfide bond had been contained as an impurity that could be confirmed by the HPLC method. This disulfide compound exhibits chemical/physical behavior similar to that of the sulfur-containing compound having a thio group, which is the object compound, and cannot be removed by practicable refining means.

Under such circumstances, formation of the disulfide compound which is a by-product can be greatly decreased by conducting the reaction of the thiol compound with the compound capable of reacting with the mercapto group in an atmosphere without substantially containing oxygen while controlling the amount of water as described above. To realize the atmosphere without containing oxygen, the reaction system may be substituted to a sufficient degree with an inert gas such as of nitrogen, helium or argon, and the reaction may be conducted in such a gaseous atmosphere. When a solvent is to be used, it is desired to remove oxygen that has been dissolved therein by de-airing. In the present invention, the atmosphere without substantially containing oxygen stands for a state where the content of oxygen in the atmosphere is not larger than 10000 ppm (1% in the atmosphere).

In conducting the reaction in the present invention, it is desired to use a solvent. By using the solvent, the basic compound which is even in a solid form dissolves partly or entirely enabling the reaction to be smoothly conducted. As described above, further, when the basic compound that is used does not almost dissolve in the starting material or in the organic solvent used for the reaction but dissolves in water, then, water is added in amount specified by the present invention to further enhance the rate of reaction.

Any known solvent can be used without limitation provided it does not adversely affect the reaction. Examples of the solvent that can be preferably used include alcohols such as methanol, ethanol, and isopropanol; ethers such as diethylether, tetrahydrofurane and dioxane; halogen compounds such as methylene chloride and chloroform; and aliphatic or aromatic hydrocarbons such as hexane, heptane, benzene and toluene. Among them, it is desired to use alcohols such as methanol, ethanol or isopropanol from the standpoint of easily dissolving the solid basic compound. When these alcohols are used, the reaction proceeds at a sufficiently large rate even without adding water. The above solvents may be used being mixed together. There is no particular limitation on the amount of using the solvent. Usually, however, the solvent is used in an amount of about 50 to about 2000 parts by weight per 100 parts by weight of the thiol compound.

In the above reaction, there is no particular limitation on the procedure of operation; i.e., into a reaction vessel that has been substituted with an inert gas in advance, there may be suitably mixed the reaction reagents, a solvent used as required and water used as required. For example, the thiol compound is dissolved in the presence of the basic compound and the reaction solvent and, then, the compound capable of reacting with the mercapto group diluted with the reaction solvent is added to the above solution, followed by stirring in an invert gas atmosphere.

When it is attempted to prepare a radically polymerizable sulfur-containing compound such as (meth)acryloyl group as a polymerizable functional group, it is desired to add a polymerization inhibitor to prevent gelation. As the polymerization inhibitor, there can be used any known compound without limitation. Concrete examples thereof include phenolic polymerization inhibitors such as hydroquinone, p-methoxyphenol, 2,6-di-t-butyl-4-methylphenol and p-t-butylcatechol; phenothiazine, copper chloride (II) and iron chloride (III). Among them, it is desired to use p-methoxyphenol and p-t-butylcatechol from the standpoint of ability for inhibiting the polymerization, coloring of the product and removing the reaction product after the reaction. The polymerization inhibitor is used in an amount that varies depending upon the kind of the inhibitor and the reaction temperature. Generally, however, the polymerization inhibitor is used in an amount of 0.01 to 10% by weight and, preferably, 0.1 to 5% by weight of the radically polymerizable sulfur-containing compound such as (meth)acryloyl group which is the object product.

The reaction conditions are not particularly limited but are generally as described below.

The reaction temperature differs depending upon the kinds and amounts of the reaction agents and solvents that are used, but is generally from −5 to 150° C. and, preferably, from 10 to 100° C. The reaction time, too, differs depending upon the kinds and amounts of the starting materials that are used, but is generally from 10 minutes to 48 hours and, preferably, from 30 minutes to 24 hours. It is desired to maintain the stirring during the reaction.

The sulfur-containing compound prepared according to the above method can be isolated by a known method. According to the above method of the present invention, the side reaction is suppressed. When the conversion of the reaction is high, therefore, all what are needed are simply to effect the filtering (when the object product is a solid) and to distill the solvent off. When the conversion is low, an excess of the basic compound is processed and, then, the unreacted reagent and, as required, the solvent may be separated by distillation or recrystallization. When even a slight degree of coloring of the object product is of a problem, the separation operation may be executed after having conducted a known refining operation such as column chromatography, treatment with an adsorbing agent such as a treatment with activated carbon, or treatment with silica, decoloring treatment such as washing by using a mother, an aqueous solution of hydrogen chloride, or an aqueous solution of sodium hydroxide.

Through the above-mentioned method, there is obtained a sulfur-containing compound having at least one thio group in the molecule and having a structure corresponding to the structure of the thiol compound and of the compound capable of reacting with the mercapto group, that are used as starting materials. For example, when the compounds represented by the above formulas (1) to (5) are used as thiol compounds and a compound represented by the above general formula (6) is used as the compound capable of reacting with the mercapto group, there are obtained sulfur-containing compounds represented by the above general formulas (7) to (11) corresponding thereto.

It is desired that the sulfur-containing compound has a polymerizable functional group in the molecules from the standpoint of using it as a polymerizable monomer for an optical material for producing photochromic plastic lenses, as described above. In the case of the sulfur-containing compounds represented by, for example, the general formulas (7) to (11), it is desired that $R^{11}$, $R^{12}$, $R^{13}$ and $R^{14}$ are alkyl groups with 1 to 4 carbon atoms having at least a polymerizable functional group or (meth)acryloyl groups as a substituent.

Concrete examples of the sulfur-containing compound represented by the above general formula (7) and derivatives thereof that can be favorably used as monomers for producing photochromic lenses according to the invention, include compounds of the following structures.

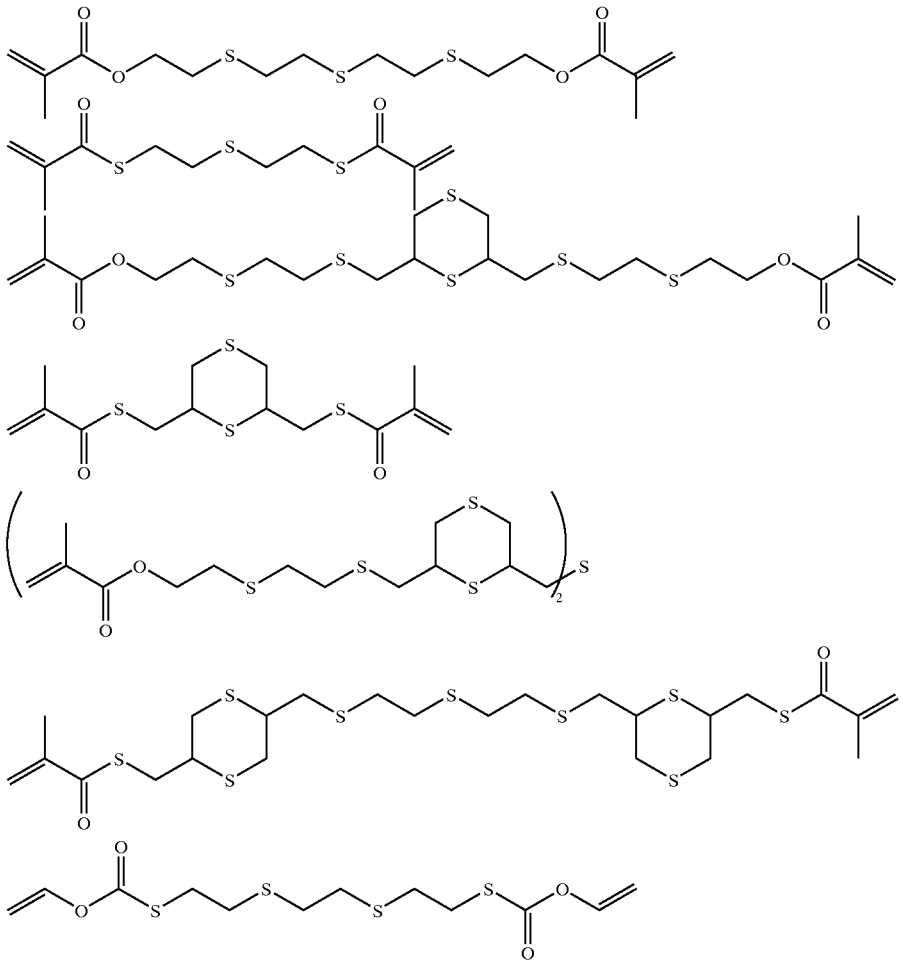

Concrete examples of the sulfur-containing compound represented by the above general formula (8) and derivatives thereof that can be favorably used as monomers for producing photochromic lenses according to the invention, include compounds of the following structures.

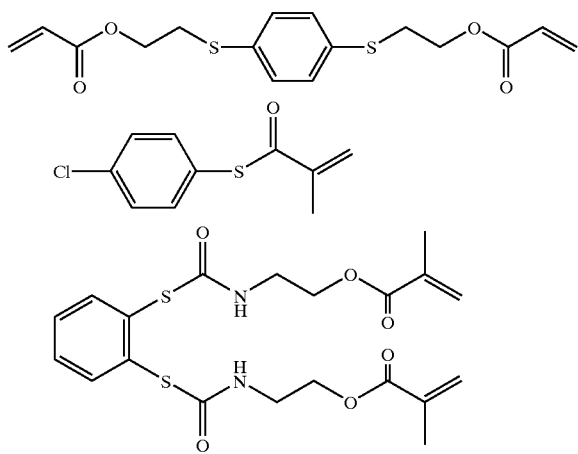

Concrete examples of the sulfur-containing compound represented by the above general formula (9) and derivatives thereof that can be favorably used as monomers for producing photochromic lenses according to the invention, include compounds of the following structures.

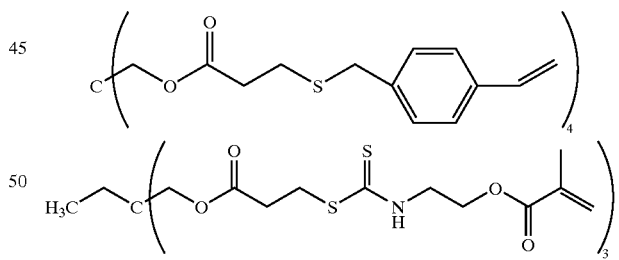

Concrete examples of the sulfur-containing compound represented by the above general formula (10) and derivatives thereof that can be favorably used as monomers for producing photochromic lenses according to the invention, include compounds of the following structures.

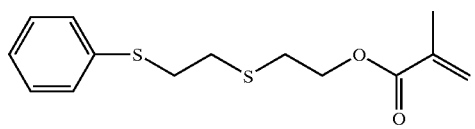

-continued

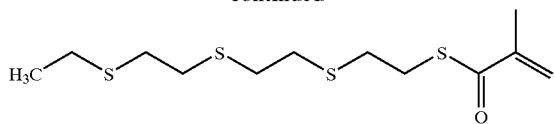

Concrete examples of the sulfur-containing compound represented by the above general formula (11) and derivatives thereof that can be favorably used as monomers for producing photochromic lenses according to the invention, include compounds of the following structures.

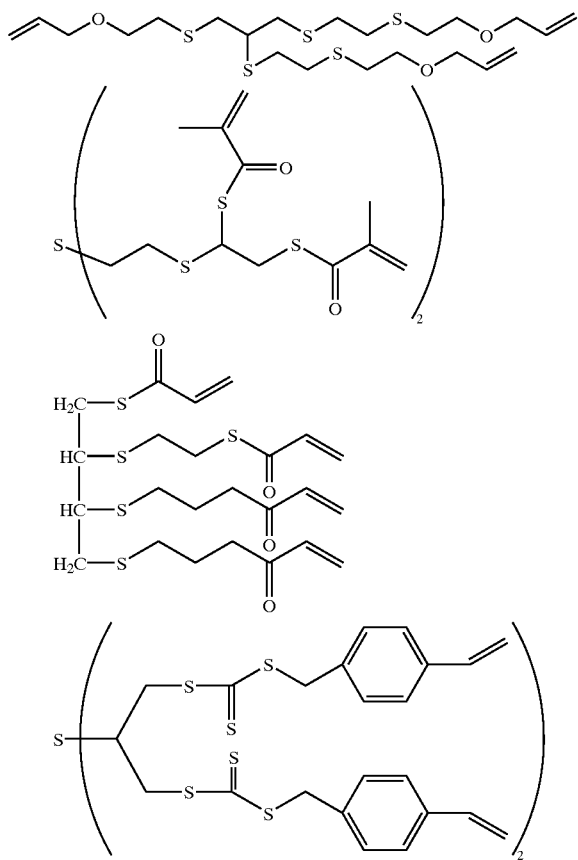

When the polymerizable functional group is a radically polymerizable group such as (meth)acryloyl group, (meth)acryloyloxy group, vinyl group, allyloxy group or styryl group, the sulfur-containing compound having such a polymerizable functional group in the molecules can be readily used as a monomer for producing photochromic plastic lenses (the monomers used for this purpose are usually cured by radical polymerization). When the polymerizable functional group is hydroxyl group, mercapto group, isocyanate group, thioisocyanate group, epoxy group, epithio group, amino group or carboxyl group, the sulfur-containing compound having such a polymerizable functional group can be used as a monomer for being ionization polymerized, for being polycondensed or for being polyadded. Or, the sulfur-containing compound may be reacted with a compound (hereinafter also referred to as a compound for introducing radically polymerizable group) having a radically polymerizable group and having a group capable of reacting with the polymerizable functional group of the sulfur-containing compound to introduce the radically polymerizable group into the sulfur-containing compound. Then, the thus obtained derivative having the radically polymerizable group introduced into the molecules can be used as a monomer for producing photochromic plastic lenses.

In the method of preparing the above derivative having a radically polymerizable group introduced into the molecules, there is no particular limitation on the compound for introducing the radically polymerizable group provided it has in the molecules thereof above a ragically polymerizable group and a group (hereinafter also referred to as functional group for introducing radically polymerizable group) that reacts with the polymerizable functional group of the sulfur-containing compound to introduce the radically polymerizable group into the sulfur-containing compound.

Here, the functional group for introducing the radically polymerizable group may be the one capable of introducing the radically polymerizable group into the sulfur-containing compound relying on a simple reaction such as addition, condensation or substitution, and is suitably selected out of the known functional groups depending upon the kind of the polymerizable functional group that is to be reacted. Concrete examples of the combination of the polymerizable functional group and the functional group for introducing the radically polymerizable group or the compound for introducing the radically polymerizable group capable of introducing the radically polymerizable group according to a customary manner, include a combination of a hydroxyl group and a halogen atom or an ester compound; a combination of a mercapto group and a halogen atom; a combination of an isocyanate group and an amino group, a hydroxyl group or a mercapto group; a combination of a thioisocyanate group and an amino group, a hydroxyl group or a mercapto group; a combination of an epoxy group and a hydroxyl group or a mercapto group; a combination of an epithio group and a hydroxyl group or a mercapto group; a combination of an amino group and a carboxyl group; and a combination of a carboxyl group and an amino group or a hydroxyl group.

Even in preparing a derivative having a radically polymerizable group introduced into the molecules by reacting the compound for introducing the radically polymerizable group with a reaction product of the thiol compound and the compound capable of reacting with the mercapto group, the thiol compound is reacted with the compound capable of reacting with the mercapto group in the preceding stage in an atmosphere without substantially containing oxygen in addition to controlling the number of moles of water contained in the reaction system to be a particular value. Then, the derivative that is obtained contains a very small amount of disulfide compound that is formed by the reaction in the preceding stage.

When the method of the present invention is conducted in the reaction atmosphere without substantially containing oxygen as described above, the obtained reaction product contains a greatly decreased amount of disulfide compound which causes a drop in the light resistance of photochromic properties of the lenses when it is used as a monomer for producing photochromic plastic lenses. The content is usually not larger than 2 mol % and can, further, be decreased to be not larger than 1 mol %.

Even when the derivative is prepared by using the above reaction product as a starting material like when the reaction product is reacted with the compound for introducing the radically polymerizable group, the obtained derivative does not almost contain the disulfide compound which is the impurity on account of the reasons described above.

According to the present invention, therefore, there is further provided a highly pure sulfur-containing compound which is a reaction product obtained by reacting a thiol compound with an organic compound having in the molecules thereof at least one functional group capable of forming a thio group upon reacting with a mercapto group, or a derivative of said reaction product, and is a sulfur-containing compound having at least one thio group in the molecules thereof, the sulfur-containing compound containing not more than 2 mol % of the compound having a disulfide bond, which is an impurity. Here, the derivative stands for a compound obtained by changing the structure of a small portion of the reaction product, i.e., stands for a compound obtained by introducing a substituent, by replacing the substituent (when the initial compound has a substituent) or by effecting a simple reaction such as addition reaction (when the initial compound has an unsaturated bond or a functional group), without affecting the basic structure thereof (e.g., without destroying the thio group).

There has not heretofore been recognized that the disulfide compound is contained as an impurity in the reaction product obtained by reacting the thiol compound with the compound capable of reacting with the mercapto group or in the derivative of the reaction product. Therefore, any particular refining has not been effected for removing the disulfide compound. Accordingly, the product or the derivative contained not smaller than 2 mol % (usually, not smaller than 5 mol %) of the disulfide compound irrespective of whether it was the one obtained by using metal sodium or the one obtained by an improved method. On the other hand, the highly pure sulfur-containing compound of the present invention is a novel one containing not more than 2 mol % of the disulfide compound, and has a feature in that when it is used as a monomer for obtaining photochromic plastic lenses, a high refractive index is exhibited without decreasing the light resistance in the photochromic property of the obtained lenses.

Next, described below is when the sulfur-containing compound of the present invention is used as a monomer for producing photochromic plastic lenses. When used for such applications, the sulfur-containing compound usually has a radically polymerizable group in the molecules.

When used for the above application, it is desired to use the sulfur-containing compound in combination with one or two or more of radically polymerizable monomers which are copolymerizable therewith from the standpoint of moldability, physical properties, optical properties and photochromic properties of the cured product that is obtained. In order that the obtained cured product exhibits a high refractive index and a high Abbe's number, it is desired that the content of the sulfur-containing compound of the invention is not smaller than 10% by weight, preferably, from 10 to 90% by weight and, particularly preferably, from 20 to 90% by weight of the weight of the whole polymerizable monomers.

Concrete examples of the compound that can be preferably used as a polymerizable monomer in combination with the sulfur-containing compound of the present invention include monofunctional (meth)acrylate polymerizable monomers such as glycidyl (meth)acrylate, β-methyl glycidyl (meth)acrylate, bisphenol A-monoglycidyl ether methacrylate, 4-glycidyloxybutyl methacrylate, 3-(glycidyl-2-oxyethoxy)-2-hydroxypropyl methacrylate, 3-(glycidyloxy-1-isopropyloxy)-2-hydroxypropyl acrylate, 3-(glycidyloxy-2-hydroxypropyloxy)-2-hydroxypropylacrylate, methyl (meth)acrylate, ethyl (meth)acrylate, butyl (meth)acrylate, isobornyl (meth)acrylate, benzyl (meth)acrylate, phenyl (meth)acrylate, tribromophenyl (meth)acrylate, 2-hydroxyethyl (meth)acrylate, phenoxyethyl(meth)acrylate, phenoxypolyethylene glycol (meth)acrylate, alkoxypolyethylene glycol (meth)acrylate, alkoxypolypropylene glycol (meth)acrylate and trifluoromethyl (meth)acrylate; monofunctional allyl ether compounds such as methoxypolyethylene glycol allyl ether, methoxypolyethylene polypropylene glycol allyl ether, butoxypolyethylene glycol polypropylene glycol allyl ether, and phenoxypolyethylene glycol allyl ether; polyfunctional (meth)acrylate polymerizable monomers such as triethylene glycol di(meth)acrylate, tetraethylene glycol di(meth)acrylate, nonaethylene glycol di(meth)acrylate, tetradecaethylene glycol di(meth)acrylate, tripropylene glycol di(meth)acrylate, tetrapropylene glycol di(meth)acrylate, nonapropylene glycol di(meth)acrylate, di(meth)acrylate of nonaethylene glycol diacrylate, polybutylene glycol di(meth)acrylate, 1,6-hexanediol di(meth)acrylate, neopentyl glycol di(meth)acrylate, acrylic acid and methacrylic ester compound of 2,2'-bis(4-methacryloyloxyethoxyphenyl)propane, acrylic acid and methacrylic ester compound of 2,2'-bis(4-methacryloyloxypolyethoxyphenyl)propane, acrylic acid and methacrylic ester compound of 2,2'-bis(4-methacryloyloxypropoxyphenyl)propane, acrylic acid and methacrylic ester compound of 2,2'-bis(4-methacryloyloxypolypropoxyphenyl)propane, acrylic acid and methacrylic ester compound of 2,2'-bis(3,5-dibromo-4-methacryloyloxyethoxy)propane, acrylic acid and methacrylic ester compound of hydrogenated bisphenol A ethylene oxide or propylene oxide adduct, dimethylol tricyclodecane di(meth)acrylate, dimethyloltricyclodecane-polyethoxy di(meth)acrylate, trimethylolpropane tri(meth)acrylate, pentaerythritol tetra(meth)acrylate, a reaction product of ethylene glycol or polyethylene glycol with glycidyl (meth)acrylate, a reaction product of propylene glycol or polypropylene glycol with glycidyl (meth)acrylate, a reaction product of bisphenol A ethylene oxide or propylene oxide adduct with glycidyl (meth)acrylate, a reaction product of hydrogenated bisphenol A ethylene oxide or propylene oxide adduct with glycidyl (meth)acrylate, and urethane acrylate; and styryl polymerizable monomers such as styrene, chlorostyrene, α-methylstyrene, α-methylstyrene dimer, vinyl naphthalene, isopropenyl naphthalene, bromostyrene and divinyl benzene. These polymerizable monomers can be used in one kind or being mixed in two or more kinds.

Upon being mixed with a photochromic compound, the polymerizable monomer composition containing the sulfur-containing compound of the invention can be used as a monomer composition for producing photochromic plastic lenses. When the sulfur-containing compound is of a highly pure form containing the disulfide compound in an amount of not larger than 2 mol %, the amount of the disulfide compound contained in the polymerizable monomer composition is not larger than 0.02 mols per mole of the highly pure sulfur-containing compound. From the standpoint of light resistance of photochromic properties in the obtained photochromic plastic lenses, it is desired that the amount of the disulfide compound contained in the polymerizable monomer composition is not larger than 0.01 mol and, particularly, not larger than 0.005 mols per mole of the sulfur-containing compound.

Any known photochromic compound that exhibits photochromic action can be mixed without any limitation to the polymerizable monomer composition. Fulgide compounds, chromene compounds and spirooxazine compounds are well-known examples of the photochromic compounds, and it is allowable to use these photochromic compounds. It is allowable to use those photochromic compounds that are disclosed in, for example, Japanese Unexamined Patent Publication (Kokai) No. 28154/1990, Japanese Unexamined Patent Publication (Kokai) No. 288830/1987 and PCT International Patent Application 96/14596.

As compounds having excellent photochromic properties, there can be further favorably used many compounds developed by the development group to which the present inventors belong (Japanese Patent Application No. 207871/1997, Japanese Patent Application No. 23110/1999, Japanese Patent Application No. 27959/1999, Japanese Patent Application No. 27961/1999, Japanese Patent Application No. 27960/1999, Japanese Patent Application No. 140836/1999, Japanese Patent Application No. 144072/1999, Japanese Patent Application No. 150690/1999, Japanese Patent Application No. 144074/1999, Japanese Patent Application No. 156270/1999, Japanese Patent Application No. 154272/1999, Japanese Patent Application No. 188146/1999, Japanese Patent Application No. 188902/1999). These photochromic compounds can be used in one kind or being mixed in two or more kinds, the blending ratio thereof being determined depending upon the use.

Among these photochromic compounds, it is particularly desired to use the chromene compounds represented by the following general formulas (18) to (25) having photochromic properties such as light resistance, color density and fading rate that are superior to those of other photochromic compounds.

A chromene compound represented by the following general formula (18),

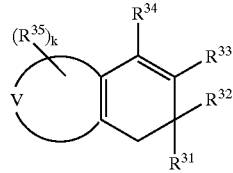

(18)

wherein a group represented by the following formula (26),

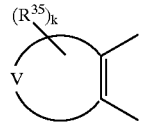

(26)

is a substituted, or unsubstituted aromatic hydrocarbon group or a substituted or unsubstituted unsaturated heterocyclic group, $R^{33}$, $R^{34}$ and $R^{35}$ are alkyl groups, alkoxy groups, aralkoxy groups, amino groups, substituted amino groups, cyano groups, substituted or unsubstituted aryl groups, halogen atoms, aralkyl groups, hydroxy groups, substituted or unsubstituted alkynyl groups, substituted or unsubstituted heterocyclic groups having a nitrogen atom as a hetero atom and in which the nitrogen atom and a pyran ring or a ring of the group represented by the above general formula (18) are bonded together, or condensed heterocyclic groups in which the heterocyclic group is condensed with an aromatic hydrocarbon ring or with an aromatic heterocyclic ring, k is an integer of 0 to 6, $R^{31}$ and $R^{32}$ are, independently from each other, groups represented by the following formula (27),

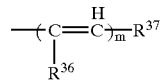

(27)

wherein $R^{36}$ is a substituted or unsubstituted aryl group or a substituted or unsubstituted heteroaryl group, $R^{37}$ is a hydrogen atom, an alkyl group or a halogen atom, m is an integer of 1 to 3, groups represented by the following formula (28),

(28)

wherein $R^{38}$ is a substituted or unsubstituted aryl group, or a substituted or unsubstituted heteroaryl group, and m' is an integer of 1 to 3, substituted or unsubstituted aryl groups, substituted or unsubstituted heteroaryl groups or alkyl groups, or $R^{31}$ and $R^{32}$ together may constitute an aliphatic hydrocarbon ring or an aromatic hydrocarbon ring.

The substituents in the substituted aryl groups or in the substituted heteroaryl groups in the above formulas (27) and (28) or denoted by $R^{31}$ and $R^{32}$ are the same as those denoted by $R^{33}$ to $R^{35}$.

A chromene compound of the following general formula (19),

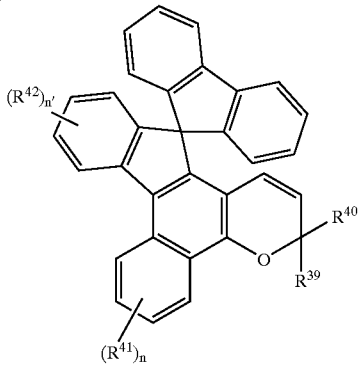

(19)

wherein $R^{39}$ and $R^{40}$ are, independently from each other, the same as those denoted by $R^{31}$ and $R^{32}$ in the above general formula (18), $R^{41}$ and $R^{42}$ are the same as those denoted by $R^{33}$, $R^{34}$ and $R^{35}$ in the above general formula (18), and n and n' are, independently from each other, integers of 0 to 4.

A chromene compound represented by the general formula (20),

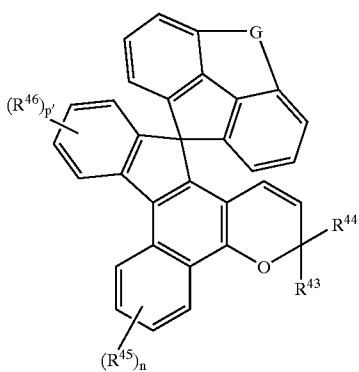

(20)

wherein $R^{43}$ and $R^{44}$ are, independently from each other, the same as those denoted by $R^{31}$ and $R^{32}$ in the above general formula (18), $R^{45}$ and $R^{46}$ are the same as those denoted by $R^{33}$, $R^{34}$ and $R^{35}$ in the above general formula (18), p and p' are, independently from each other, integers of 0 to 4, and G is any one of the group represented by the following general formulas,

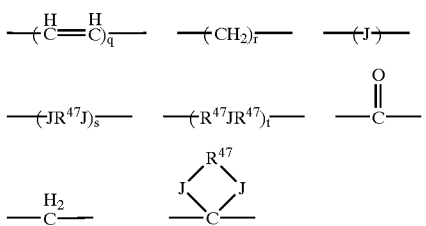

wherein J is an oxygen atom or a sulfur atom, $R^{47}$ is an alkylene group with 1 to 6 carbon atoms, and q, r, s and t are, independently from each other, integers of 1 to 4.

A chromene compound represented by the general formula (21),

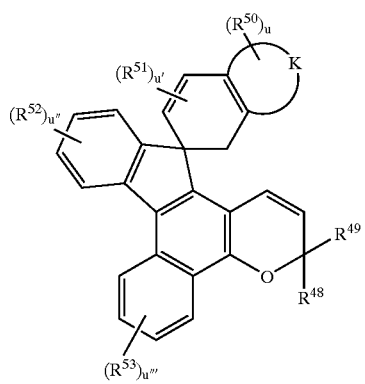

(21)

wherein $R^{48}$ and $R^{49}$ are, independently from each other, the same as those denoted by $R^{31}$ and $R^{32}$ in the above general formula (18), $R^{50}$, $R^{51}$, $R^{52}$ and $R^{53}$ are the same as those denoted by $R^{33}$, $R^{34}$ and $R^{35}$ in the above general formula (18), u is an integer of 0 to 6, u', u" and u'" are, independently from each other, integers of 0 to 4, and the following formula (29)

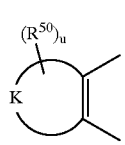

(29)

represents a substituted or unsubstituted aromatic hydrocarbon group, or a substituted or unsubstituted unsaturated heterocyclic group.

A chromene compound represented by the general formula (22),

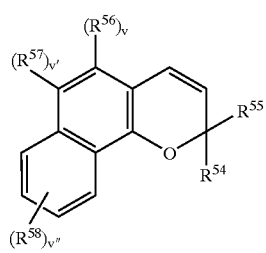

(22)

wherein $R^{54}$ and $R^{55}$ are, independently from each other, the same as those denoted by $R^{31}$ and $R^{32}$ in the above general formula (18), $R^{56}$, $R^{57}$ and $R^{58}$ are the same as those denoted by $R^{33}$, $R^{34}$ and $R^{35}$ in the above general formula (18), v' and v" are, independently from each other, integers of 0 or 1, and v'" is an integer of 0 to 4.

A chromene compound represented by the general formula (23),

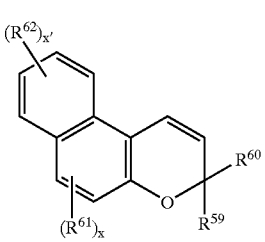

(23)

wherein $R^{59}$ and $R^{60}$ are, independently from each other, the same as those denoted by $R^{31}$ and $R^{32}$ in the above general formula (18), $R^{61}$ and $R^{62}$ are the same as those denoted by $R^{33}$, $R^{34}$ and $R^{35}$ in the above general formula (18), x is an integer of 0 to 2, and x' is an integer of 0 to 4.

A chromene compound represented by the general formula (24),

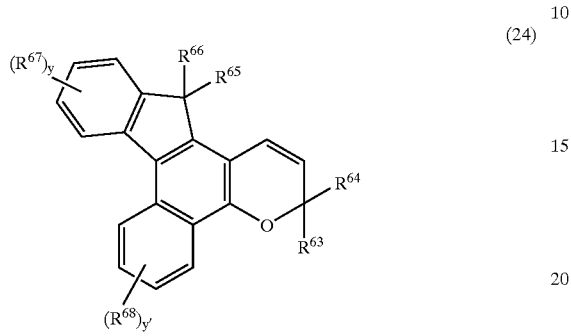

(24)

wherein $R^{63}$ and $R^{64}$ are, independently from each other, the same as those denoted by $R^{31}$ and $R^{32}$ in the above general formula (18), $R^{65}$, $R^{66}$, $R^{67}$ and $R^{68}$ are the same as those denoted by $R^{33}$, $R^{34}$ and $R^{35}$ in the above general formula (18), and y and y' are, independently from each other, integers of 0 to 4.

A chromene compound represented by the general formula (25),

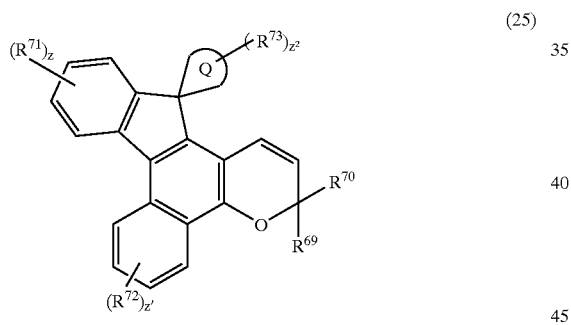

(25)

wherein $R^{69}$ and $R^{70}$ are, independently from each other, the same as those denoted by $R^{31}$ and $R^{32}$ in the above general formula (18), $R^{71}$, $R^{72}$ and $R^{73}$ are the same as those denoted by $R^{33}$, $R^{34}$ and $R^{35}$ in the above general formula (18), and z and z' are, independently from each other, integers of 0 to 4, z''' is an integer of 0 to 6, and the following formula (30)

(30)

represents an aliphatic hydrocarbon ring that may have up to 6 substituents.

The chromene compounds that can be particularly favorably used in the present invention are those compounds having structures as described below.

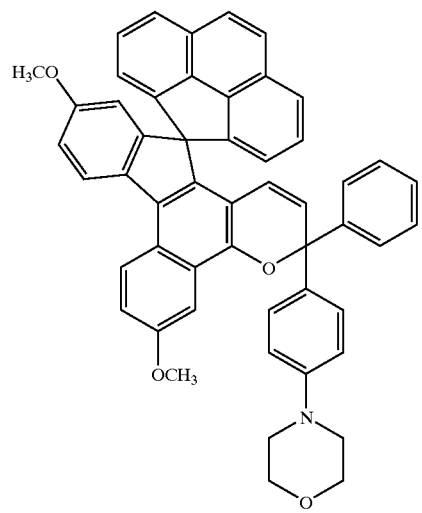

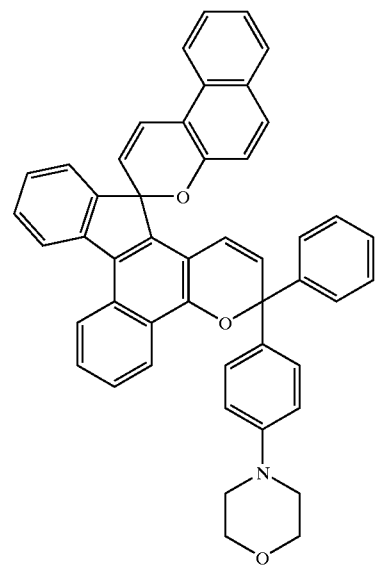

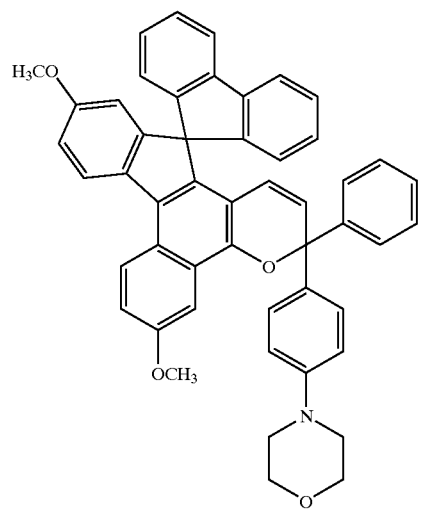

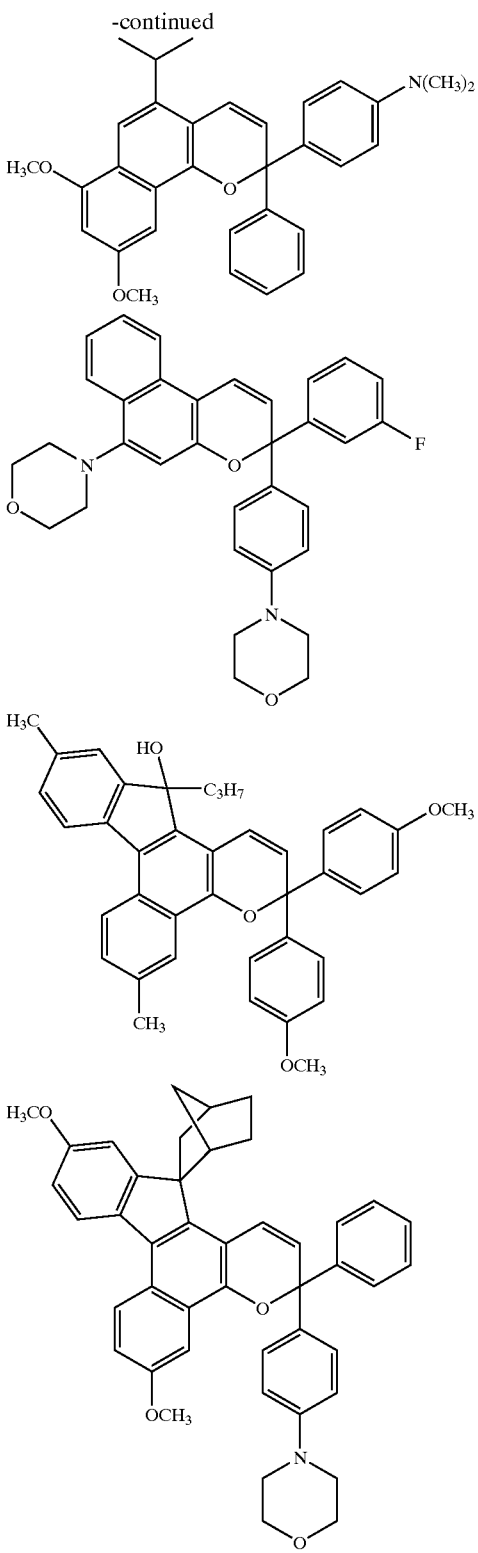

In the photochromic polymerization-curable composition of the present invention, there is no particular limitation on the ratio of blending the photochromic compound. From the standpoint of photochromic properties and initial color of the cured product (color of when not irradiated with light, i.e., color in a dark place), however, it is desired to blend the photochromic compound in an amount of from 0.0001 to 10 parts by weight, more preferably, from 0.001 to 5 parts by weight and, particularly preferably, from 0.001 to 1 part by weight per 100 parts by weight of the whole polymerizable monomers.

In order to improve the light resistance of the photochromic compound, to improve the color density, to improve the fading rate and to improve the moldability, the photochromic polymerization-curable composition of the present invention may be further blended, as required, with various stabilizers and additives being mixed together, such as parting agent, antioxidizing agent, radical-trapping agent, ultraviolet ray absorber, infrared ray absorber, ultraviolet ray stabilizer, antioxidant, coloring-preventing agent, antistatic agent, surfactant, fluorescent dye, dye, pigment, perfume, and plasticizer.

When the ultraviolet ray stabilizer is mixed into the photochromic polymerization-curable composition of the present invention, the light resistance of the photochromic compound is further improved, which is favorable. As the ultraviolet ray stabilizer, there can be favorably used a hindered amine photo-stabilizer, hindered phenol photo-stabilizer, and sulfur-type antioxidant. Though there is no particular limitation, the ultraviolet ray stabilizer is usually used in an amount of from 0.001 to 10 parts by weight and, more preferably, from 0.01 to 1 part by weight per 100 parts by weight of the whole polymerizable monomers.

Upon mixing the infrared ray absorber, further, there can be obtained a photochromic cured product which exhibits infrared ray-absorbing property in addition to exhibiting photochromic action. As the infrared ray-absorber, there can be used a polymethine compound, a diimonium compound, a cyanin compound, an anthraquinone compound and an aluminum compound. Among them, however, the diimonium compound is preferred having a large molar extinction coefficient and exhibiting the effect by the addition in a small amount. It is desired that the infrared ray absorber is blended in an amount of from 0.0001 to 1 part by weight and, particularly, from 0.001 to 0.01 part by weight per 100 parts of the whole polymerizable monomers.

There is no particular limitation on the method of preparing the photochromic polymerization-curable composition of the invention, and the composition can be prepared by weighing and mixing the individual components in predetermined amounts. There is no particular limitation on the order of adding the individual components. All of the components may be added at the same time, or the monomer components may be mixed, first, and then the photochromic compound and other additives may be added just before being polymerized. As required, the polymerization initiator may be added in conducting the polymerization.

There is no particular limitation on the polymerization method for obtaining a cured product from the photochromic polymerization-curable composition of the invention, and any known radical polymerization method may be employed depending upon the kind of the monomer that is used. The polymerization can be initiated by using various radical polymerization initiators such as peroxides or azo compounds, or by the irradiation with ultraviolet rays, α-rays, β-rays or γ-rays, or by a combination thereof.

To obtain a cured product used as a photochromic plastic lens, for example, there can be favorably employed a cast polymerization in which the photochromic polymerization-curable composition of the invention mixed with a radical polymerization initiator is poured into between the elastomer gaskets or the molds held by spacers, cured by polymerization in an air furnace and is, then, taken out from the molds.

Here, any known radical polymerization initiator can be used without particular limitation. Its representative examples include diacyl peroxides such as benzoyl peroxide, p-chlorobenzoyl peroxide, decanoyl peroxide, lauroyl peroxide, and acetyl peroxide; peroxy esters such as t-butylperoxy-2-ethyl hexanate, t-butylperoxy neodecanate, cumylperoxy neodecanate and t-butylperoxy benzoate; percarbonates such as diisopropylperoxy dicarbonate, and di-sec-butylperoxy dicarbonate; and azo compounds such as azobisisobutilonitrile.

The amount of using the radical polymerization initiator varies depending upon the polymerization conditions, kind of the initiator and the composition of the monomers, and cannot be exclusively specified. Generally, however, the radical polymerization initiator is used in an amount of from 0.001 to 10 parts by weight and, preferably, from 0.01 to 5 parts by weight per 100 parts by weight of the whole polymerizable monomers.

In carrying out the cast polymerization, the polymerization temperature seriously affects the properties of the obtained photochromic cured product. Optimum temperature conditions cannot be exclusively specified as they are affected by the kind and amount of the initiator and by the kind of the monomer. Generally, however, it is desired to employ a so-called taper-type two-stage polymerization in which the polymerization starts at a relatively low temperature, the temperature is gradually elevated and the polymerization is completed at a high temperature to effect the curing. Like the temperature, the polymerization time, too, differs depending upon a variety of factors, and it is desired to determine, in advance, an optimum time depending upon these conditions. In general, however, it is desired to so select the conditions that the polymerization is completed in 2 to 40 hours.

In the foregoing was described the cast polymerization by using the radical polymerization initiator. It is, however, also possible to conduct the cast polymerization in the same manner by using the photopolymerization initiator. The photopolymerization initiator that can be used include benzoin, benzoinmethyl ether, benzoinbutyl ether, benzophenol, acetophenone-4,4'-dichlorobenzophenone, diethoxyacetophenone, 2-hydroxy-2-methyl-1-phenylpropane-1-one, benzylmethyl ketal, 1-(4-isopropylphenyl)-2-hydroxy-2-methylpropane-1-one, 1-hydroxycyclohexylphenyl ketone, and 2-isopropylthioxanthone. Generally, these photopolymerization initiators are used in an amount of from 0.001 to 5 parts by weight per 100 parts by weight of the whole polymerizable monomers.

The photochromic cured product of the invention obtained by the above method can be put to the following treatment depending upon the field of use. That is, dying by using a dye such as dispersion dye; reflection-preventing treatment by forming an organic high molecular thin film by applying a hard coating agent comprising, chiefly, a sol such as silane coupling agent, silicon, zirconium, antimony, aluminum, tin or tungsten, or by forming a thin film by vaporizing a metal oxide such as $SiO_2$, $TiO_2$ or $ZrO_2$; or antistatic treatment.

EXAMPLES

The invention will now be described by way of Working Examples to which only, however, the invention is in no way limited.

In Examples 1 to 21 and in Comparative Examples 1 to 3 among all of Examples and Comparative Examples, the sulfur-containing compounds having at least one thio group in the molecules were determined for their purities by using a gas chromatography (purity I: containing a disulfide compound which is an impurity). In these Examples and Comparative Examples were further determined, by the gas chromatography, the contents of by-products having, in the molecules, thio groups (hereinafter simply referred to as by-products) in amounts smaller than those of the sulfur-containing compound which is the object product.

In Examples 22 to 38, the sulfur-containing compounds having at least one thio group and at least one polymerizable functional group in the molecules were measured for their purities by using a high-speed liquid chromatography (HPLC method)(purity II). In these Examples and Comparative Examples, further, the content of the disulfide compound was also determined by the high-speed liquid chromatography.

The color of the product was evaluated by eyes by isolating the sulfur-containing compound obtained by the reaction without refining it and dissolving it in an N,N-dimethyl sulfoxide solution in an amount of 5% by weight. The basis of evaluation was as follows:

○: Colorless or faintly yellow.
Δ: Slightly yellow
X: Yellow

Example 1

150 Grams (0.974 mols) of a 2-mercaptoethyl sulfide that is a starting thiol compound was heated and stirred in 1000 ml of methanol (solvent) in the presence of 77.9 g (1.948 mols) of sodium hydroxide that is a basic compound at 40° C. for 30 minutes. To this solution was then added dropwise a solution of 164.7 g (2.045 mols) of a 2-chloroethanol which is a compound capable of reacting with a mercapto group and 150 ml of methanol. Since heat generates during the dropwise addition, the dropping operation was carefully conducted such that the reaction temperature did not exceed 60° C. After the dropwise addition has been finished, the solution was stirred at 40° C. for 3 hours and the temperature was, then, raised to 60° C.

Then, NaCl which is a by-product of the reaction was removed by filtering while it was still hot, and the filtrate was cooled in an ice bath to obtain a sulfur-containing compound having a thio group in the molecules (hereinafter also referred to simply as formed sulfur-containing compound) represented by the following structural formula (A) maintaining an yield of 215.2 g (0.889 mols). The yield of isolation was 91.3% and the purity I was 98.9% as measured by gas chromatography. The yield of isolation used here is a value on the basis of the starting thiol compound.

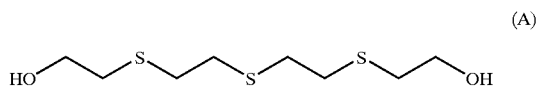
(A)

The amount of water in the reaction was measured by the Karl Fischer's method, and it was found that the amount of water was about 1000 ppm (about 0.03 times of the mole number of the starting mercapto groups; hereinafter, the mol number of water for the mol number of the starting mercapto group is also simply referred to as "water molar ratio") at the start of the reaction and was about 40,000 ppm (about 1.1 times of the mole number of the starting mercapto groups, i.e., a water molar ratio of about 1.1) at the end of the reaction. The amount of water has increased due to the formation of water by the reaction of hydrogen chloride with sodium hydroxide.

The formed product was examined for its color. However, almost no color was observed and the product was nearly in a colorless state (evaluation: ○).

Examples 2 to 21

Sulfur-containing compounds shown in Tables 1 and 2 were synthesized by using the starting thiol compounds and the compounds capable of reacting with mercapto groups shown in Tables 1 and 2, and by conducting the reaction in the same manner as in Example 1 but changing the reaction conditions as shown in Tables 3 and 4. Conversions of the reactions (based on the starting thiol compounds), amounts of by-products, yields of isolation of the formed sulfur-containing compounds, purities I and evaluated results of colors, were as shown in Tables 3 and 4.

In all of the Examples, by-products were formed little, and sulfur-containing compounds having high purities were obtained maintaining high yields of isolation as measured by gas chromatography. The isolated sulfur-containing compounds did not almost exhibit color, and their coloring properties were evaluated to be favorable.

Comparative Examples 1 to 3

The reaction was conducted in the same manner as in Example 1 but using the solvents shown in Table 4. The results were as shown in Table 4.

As demonstrated by the results of Comparative Examples 1 to 3, when the reaction was conducted under the conditions in which water existed in large amounts in the reaction system, by-products were formed in large amounts. In particular, when water was used as a reaction solvent (Comparative Example 2), the formed sulfur-containing compound which was the object product was colored to a considerable degree.

TABLE 1

| Example | Thiol compound | Compound capable of reacting with mercapto group | Formed S-containing compound |
|---|---|---|---|
| 1, 2, 3, 4, 5 | HS–CH₂CH₂–S–CH₂CH₂–SH | Cl–CH₂CH₂–OH | HO–CH₂CH₂–S–CH₂CH₂–S–CH₂CH₂–S–CH₂CH₂–OH |
| 6 | HS–CH₂CH₂–S–CH₂CH₂–SH | Cl–CH₂–COOH | HOOC–CH₂–S–CH₂CH₂–S–CH₂CH₂–S–CH₂–COOH |
| 7 | HS–CH₂CH₂–S–CH₂CH(SH)–CH₂–S–CH₂CH₂–SH | Cl–CH₂CH₂–O–CH₂CH₂–OH | HO–CH₂CH₂–O–CH₂CH₂–S–(...)–S–CH₂CH₂–O–CH₂CH₂–OH |
| 8 | (p-C₆H₄)(SH)₂ (benzene-1,4-dithiol type) | Br–CH₂CH₂–OH | (p-C₆H₄)(S–CH₂CH₂–OH)₂ |
| 9, 10, 11, 12, 13 | dithiane with CH₂SH substituents | Cl–CH₂CH₂–OH | dithiane with –CH₂–S–CH₂CH₂–OH substituents |
| 14 | dithiane with CH₂SH substituents | Cl–CH₂CH₂–CH₃ | dithiane with –CH₂–S–CH₂CH₂–CH₃ substituents |

TABLE 2

| Example | Thiol compound | Compound capable of reacting with mercapto group | Formed S-containing compound |
|---|---|---|---|
| 15 | (dithiane with CH2SH groups) | Br-CH2CH2-OH | (dithiane with -CH2-S-CH2CH2-OH groups) |
| 16 | (dithiane with -SCH2CH2SH groups) | Cl-CH2CH2-OH | (dithiane with -S(CH2)2-S-CH2CH2-OH groups) |
| 17 | (bis-dithiane with SH) | Cl-CH2CH2-OH | (bis-dithiane with S-CH2CH2-OH) |
| 18 | (bis-dithiane structure with SH) | Cl-CH2CH2-OH | (bis-dithiane structure with S-CH2CH2-OH) |
| 19 | HS-(C)4- | Cl-CH2CH2-OH | HO-CH2CH2-S-(C)4- |
| 20 | HS-(C)3-C(C2H5)- | Cl-CH2CH2-OH | HO-CH2CH2-S-(C)3-C(C2H5)- |
| 21 | PhCH2-S-CH2CH2-SH | Cl-CH2CH2-OH | PhCH2-S-CH2CH2-S-CH2CH2-OH |

TABLE 3

| Ex. | Basic compound | Reaction solvent | Water molar ratio Before reaction | Water molar ratio After reaction | Reaction temp. (° C.) | Reaction time (H) | Conversion (%) | Re-product (%) | Isolation yield (%) | Purity I (%) | Color |
|---|---|---|---|---|---|---|---|---|---|---|---|
| 1 | sodium hydroxide | methanol | 0.03 | 1.1 | 50 | 3.0 | 98.6 | 0.5 | 91.3 | 98.9 | ○ |
| 2 | sodium hydroxide | methanol + water | 1.0 | 2.1 | 50 | 3.0 | 97.7 | 1.0 | 90.2 | 98.4 | ○ |
| 3 | sodium hydroxide | methanol + water | 3.0 | 4.0 | 50 | 3.0 | 97.1 | 1.4 | 89.1 | 98.3 | ○ |
| 4 | sodium hydroxide | methanol + water | 5.0 | 6.1 | 50 | 3.0 | 96.2 | 1.9 | 87.8 | 98.1 | ○ |
| 5 | sodium hydroxide | methanol + water | 6.3 | 7.4 | 50 | 3.0 | 95.5 | 2.2 | 87.5 | 97.8 | ○ |
| 6 | sodium methoxide | methanol | 0.03 | 0.05 | 50 | 2.5 | 96.3 | 0.5 | 88.3 | 98.6 | ○ |
| 7 | sodium hydroxide | chloroform + water | 2.2 | 3.2 | 50 | 2.0 | 92.4 | 0.8 | 83.8 | 95.6 | ○ |
| 8 | potassium carbonate | methanol + water | 2.5 | 2.6 | 45 | 2.5 | 93.8 | 0.8 | 83.1 | 98.3 | ○ |
| 9 | sodium hydroxide | methanol | 0.03 | 1.1 | 50 | 3.0 | 98.3 | 0.4 | 90.7 | 99.1 | ○ |
| 10 | sodium hydroxide | methanol + water | 1.0 | 2.1 | 50 | 3.0 | 97.5 | 0.8 | 91.5 | 99.0 | ○ |
| 11 | sodium hydroxide | methanol + water | 3.0 | 4.1 | 50 | 3.0 | 96.8 | 1.3 | 90.3 | 98.5 | ○ |
| 12 | sodium hydroxide | methanol + water | 5.0 | 5.0 | 50 | 3.0 | 96.1 | 1.6 | 89.5 | 98.6 | ○ |
| 13 | sodium hydroxide | methanol + water | 6.3 | 7.3 | 50 | 3.0 | 96.4 | 2.1 | 88.7 | 98.8 | ○ |
| 14 | sodium ethoxide | ethanol | 0.03 | 0.04 | 40 | 2.5 | 97.3 | 0.5 | 85.7 | 98.4 | ○ |

TABLE 4

| Ex. | Basic compound | Reaction solvent | Water molar ratio Before reaction | Water molar ratio After reaction | Reaction temp. (° C.) | Reaction time (H) | Conversion (%) | Re-product (%) | Isolation yield (%) | Purity I (%) | Color |
|---|---|---|---|---|---|---|---|---|---|---|---|
| 15 | sodium carbonate | benzene + water | 1.6 | 1.6 | 70 | 1.5 | 95.6 | 0.8 | 87.6 | 97.8 | ○ |
| 16 | sodium methoxide | methanol | 0.02 | 0.04 | 55 | 2.0 | 95.2 | 0.6 | 85.1 | 98.6 | ○ |
| 17 | sodium hydroxide | ethanol | 0.02 | 1.1 | 60 | 2.0 | 94.8 | 0.5 | 90.2 | 98.8 | ○ |
| 18 | sodium hydroxide | methanol | 0.03 | 1.2 | 50 | 2.5 | 96.6 | 0.5 | 82.8 | 97.2 | ○ |
| 19 | sodium methoxide | methanol | 0.02 | 0.03 | 40 | 4.0 | 96.0 | 0.4 | 84.6 | 98.3 | ○ |
| 20 | sodium hydroxide | toluene + water | 1.8 | 2.9 | 50 | 3.0 | 95.3 | 0.9 | 88.2 | 96.3 | ○ |
| 21 | sodium hydroxide | methanol | 0.03 | 1.0 | 50 | 2.0 | 97.2 | 0.4 | 91.3 | 99.1 | ○ |
| Comp. Ex.1 | sodium hydroxide | methanol + water | 15.0 | 16.1 | 50 | 3.0 | 89.7 | 6.3 | 81.4 | 93.4 | Δ |
| Comp. Ex.2 | sodium hydroxide | water | 28.5 | 29.5 | 50 | 3.0 | 86.6 | 10.6 | 80.2 | 91.8 | X |
| Comp. Ex.3 | sodium hydroxide | toluene + water | 15.0 | 16.0 | 50 | 3.0 | 90.3 | 5.7 | 78.9 | 93.6 | Δ |

Example 22

The following operation was all carried out in a nitrogen atmosphere unless stated otherwise. 111.8 Grams (2.790 mols) of sodium hydroxide as a basic compound and 1300 ml of dehydrated methanol (solvent) were added into a 2000-ml four-way flask with stirring at room temperature to prepare a homogeneous solution. 200 Grams (1.299 mols) of a 2-mercaptoethyl sulfide that is a thiol compound was added dropwise to the solution while cooling the solution in a water bath. After the dropwise addition has been finished, the solution was stirred at 40° C. for 30 minutes to obtain a homogeneous solution. To the solution was then added dropwise a mixture solution of 219.6 g (2.728 mols) of a 2-chloroethanol as a halogeno alcohol which is a compound capable of reacting with the mercapto group and 200 ml of dehydrated methanol. Since heat generates during the dropwise addition, the dropping operation was carefully conducted such that the reaction temperature did not exceed 60° C. After the dropwise addition has been finished, the solution was stirred at 60° C. for one hour.

Then, NaCl which is a by-product of the reaction was removed in the open air by filtering while it was still hot, and the filtrate was cooled in an ice bath to obtain a highly pure sulfur-containing compound of the invention {compound (A)} having two hydroxyl group in the molecules represented by the following structural formula (A) maintaining an yield of 294.8 g (1.218 mols). The yield of isolation was 93.8% and the purity II was 99.0% as measured by the high-speed liquid chromatography. The content of the disulfide compound contained in the compound (A) was 0.0 mol %. The yield of isolation used here is a value on the basis of the 2-mercaptoethyl sulfide which is a thiol compound.

Further, 200 g (0.826 mols) of the above compound, 4.0 g of cesium carbonate, 250 g (2.5 mols) of methyl methacrylate, 4.0 g of p-methoxy-phenol and 80 ml of hexane were fed, heated at 90° C. to conduct the reaction for 20 hours while removing methanol by azeotropy together with hexane. Thereafter, the solid matter was removed, washed with a 5% sodium hydroxide aqueous solution, water and a 20% sodium chloride aqueous solution, followed by distillation of a solvent, thereby to obtain 287.2 g (0.760 mols) of the following compound (B) which is a derivative of the above compound (A) and also is a highly pure sulfur-containing compound of the invention. The yield was 92.0%, the purity II was 95.4%, and the content of the disulfide compound contained in the compound (B) was 0.0 mol %. Here, the yield that is used is a value on the basis of the compound (A) which is a starting material.

(B)

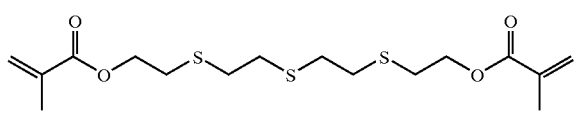

Examples 23 to 34

Thiol compounds having the structures shown in Tables 5 to 8 and the compounds capable of reacting with the mercapto group were reacted as starting materials under the reaction conditions shown in Table 10 to synthesize "sulfur-containing compounds having at least one thio group and at least one polymerizable functional group in the molecules" (polymerizable sulfur-containing compounds) shown in Tables. The yields of isolation of the reactions, purities II and the amounts of the disulfide compound were as shown in Table 10.

In Tables 5 to 8, when two kinds of compounds are described in the column of the compound that reacts with the mercapto group, it means that the compound of the upper stage was reacted, first, and, then, the obtained polymerizable sulfur-containing compound was reacted with the compound of the lower stage to obtain a highly pure sulfur-containing compound of the invention which is a derivative of the above polymerizable sulfur-containing compound. In this case, the reaction conditions shown in Table 10 stand for the reaction of the first stage. However, the purities II, the contents and the yields of the disulfide compound in Table 10 are those of the results of when the final compounds were obtained.

In all of the Examples, the content of the disulfide compound was not larger than 2 mol %, and the highly pure sulfur-containing compounds of the invention had been obtained maintaining high yields of isolation.

Examples 35 to 38

By using the starting materials shown in Tables 8 and 9, the reaction was conducted under the reaction conditions shown in Table 10. In Table 10, the reaction solvents were all those that had been fully dehydrated. The reaction was conducted in the presence of the air. The results were as shown in Table 10.

The reactions of Examples 35 to 38 were all those conducted in the presence of oxygen. Though the polymerizable sulfur-containing compounds were obtained in considerably high yields, the contents of the disulfide compound were as large as 5 mol % or more as demonstrated by the results of Table 10.

TABLE 5

| Example | Starting material | | Polymerizable S-containing compound |
|---|---|---|---|
| | Thiol compound | Compound capable of reacting with mercapto group | |
| 22 | | | |
| 23 | | | |
| 24 | | | |
| 25 | | | |

TABLE 6

| Example | Starting material | | Polymerizable S-containing compound |
|---|---|---|---|
| | Thiol compound | Compound capable of reacting with mercapto group | |
| 26 | [structure] | [structure with Cl, OH] / [structure with OCH₃, C=O] | [structure] |
| 27 | [structure] | [structure with Cl, C=O] | [structure] |
| 28 | [structure] | [structure with Cl, OH] / [structure with OH, C=O] | [structure] |
| 29 | [structure] | [structure with Cl, C=O] | [structure] |

TABLE 7

| Example | Starting material Thiol compound | Compound capable of reacting with mercapto group | Polymerizable S-containing compound |
|---|---|---|---|
| 30 | HS~S~SH | phenyl oxirane | CH2=C(CH3)C(O)O-CH(Ph)-CH2-S-CH2CH2-S-CH2CH2-S-CH2-CH(Ph)-OC(O)C(CH3)=CH2 |
| 31 | PhCH2-S-CH2CH2-SH | methacryloyl chloride; 2-chloroethanol | PhCH2-S-CH2CH2-S-CH2CH2-O-C(O)C(CH3)=CH2 |
| 32 | HS-CH2-CH(S-CH2CH2-SH)-S-CH2CH2-SH | methacrylic acid; 2-chloroethanol; allyl chloride | CH2=CH-CH2-O-CH2CH2-S-CH2-CH(S-CH2CH2-S-CH2CH2-O-CH2-CH=CH2)-S-CH2CH2-S-CH2CH2-O-CH2-CH=CH2 |
| 33 | [C(=O)-CH2CH2-SH]4 | 4-(chloromethyl)styrene | [C(-O-C(O)-CH2CH2-S-CH2-C6H4-CH=CH2)]4 |

TABLE 8

| Example | Starting material Thiol compound | Compound capable of reacting with mercapto group | Polymerizable S-containing compound |
|---|---|---|---|
| 34 | [S-CH2CH2-S-CH(SH)-CH2-SH]2 | methacryloyl chloride | [S-CH2CH2-S-CH(S-C(O)C(CH3)=CH2)-CH2-S-C(O)C(CH3)=CH2]2 |
| 35 | HS-CH2CH2-S-CH2CH2-SH | 2-chloroethanol | CH2=C(CH3)C(O)O-CH2CH2-S-CH2CH2-S-CH2CH2-S-CH2CH2-OC(O)C(CH3)=CH2 |

TABLE 8-continued

| | Starting material | | |
|---|---|---|---|
| Example | Thiol compound | Compound capable of reacting with mercapto group | Polymerizable S-containing compound |
| | | methyl methacrylate (CH₂=C(CH₃)C(=O)OCH₃) | |

TABLE 9

| | Starting material | | |
|---|---|---|---|
| Example | Thiol compound | Compound capable of reacting with mercapto group | Polymerizable S-containing compound |
| 36 | HS−CH₂CH₂−S−CH₂CH₂−SH | methacryloyl chloride | bis(methacryloylthioethyl) sulfide |
| 37 | 2,6-bis(mercaptomethyl)-1,4-dithiane | methacryloyl chloride | 2,6-bis(methacryloylthiomethyl)-1,4-dithiane |
| 38 | HS−CH₂CH₂−S−CH₂CH₂−SH | styrene oxide + methacryloyl chloride | corresponding bis-methacrylate |

TABLE 10

| Example | Reaction temp. (° C.) | Reaction solvent | Basic compound | Atmosphere | Purity II (%) | Content of disulfide compound (mol %) | Isolation yield (%) |
|---|---|---|---|---|---|---|---|
| 22 | 60 | methanol | NaOH | nitrogen | 95.4 | 0.0 | 90.1 |
| 23 | 30 | ethanol | pyridine | nitrogen | 98.1 | 0.0 | 92.4 |
| 24 | 60 | methanol | NaOMe | nitrogen | 93.8 | 0.0 | 87.3 |
| 25 | 25 | ethanol | pyridine | nitrogen | 94.5 | 0.1 | 92.8 |
| 26 | 60 | methanol | NaOH | nitrogen | 92.1 | 0.0 | 88.5 |
| 27 | 30 | methanol | pyridine | nitrogen | 93.5 | 0.0 | 86.2 |
| 28 | 65 | methanol | KOH | nitrogen | 97.4 | 0.0 | 89.7 |
| 29 | 30 | chloroform | pyridine | nitrogen | 91.3 | 0.2 | 88.9 |
| 30 | 55 | methanol | NaOMe | nitrogen | 92.0 | 0.0 | 85.7 |
| 31 | 50 | ethanol | NaOEt | nitrogen | 91.7 | 0.0 | 88.4 |
| 32 | 80 | toluene | NaOH | nitrogen | 90.1 | 0.5 | 83.4 |
| 33 | 60 | methanol | potassium carbonate | nitrogen | 91.4 | 0.3 | 91.2 |
| 34 | 30 | ethanol | pyridine | nitrogen | 93.3 | 0.0 | 86.4 |
| 35 | 60 | methanol | NaOH | air | 85.2 | 5.0 | 78.5 |

TABLE 10-continued

| Example | Reaction temp. (° C.) | Reaction solvent | Basic compound | Atmosphere | Purity II (%) | Content of disulfide compound (mol %) | Isolation yield (%) |
|---|---|---|---|---|---|---|---|
| 36 | 30 | ethanol | pyridine | air | 83.4 | 6.2 | 76.8 |
| 37 | 25 | ethanol | pyridine | air | 87.3 | 5.4 | 74.3 |
| 38 | 55 | methanol | NaOMe | air | 86.8 | 5.2 | 72.9 |

Example 39

The polymerizable sulfur-containing compound prepared in Example 22 was used as the component A and various comonomers (component B) were added to prepare a polymerizable composition comprising 78% by mass of the component A, 4% by mass of a trimethylolpropane trimethacrylate (TMPT), 2% by mass of a methoxypolyethylene glycol allylether having an average molecular weight of 550 (ALMePEG (550)), 1% by mass of a triethylene glycol diacrylate (3EGA), 4% by mass of a glycidyl methacrylate (GMA), 6% by mass of an α-methylstyrene (MS), 3% by mass of an α-methylstyrene dimer (MSD) and 2% by eight of a divinyl benzene (DVB). To 100 parts by weight of the above polymerizable composition were added 0.03 parts by weight of a chromene 1 represented by the following general formula as a photochromic compound (component C),

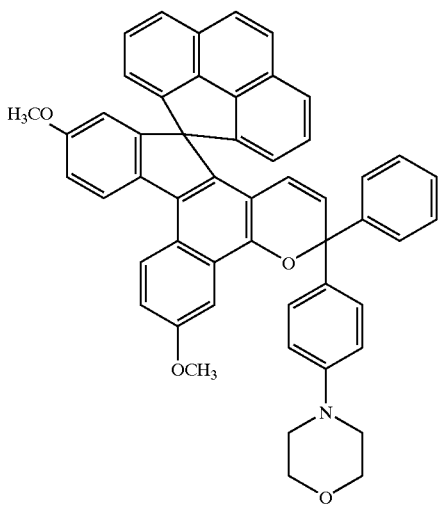

and 1.0 part by weight of a t-butylperoxy neodecanate as a radical polymerization initiator, which were mixed well to prepare a photochromic polymerization-curable composition. Next, the thus obtained composition was poured into a mold constituted by glass plates and a gasket of an ethylene/vinyl acetate copolymer to execute the cast polymerization. The polymerization was conducted by using an air furnace while gradually raising the temperature from 33° C. to 90° C. over a period of 17 hours and the temperature was maintained at 90° for 2 hours. After the polymerization, the mold was taken out from the air furnace, left to cool, and the cured product was removed from the glass mold.

The photochromic cured product (2 mm thick) of the invention obtained as described above was irradiated with light by using a xenon lamp L-2480 (300W) SHL-100 manufactured by Hamamatsu Photonics Co. through an aeromass filter (manufactured by Corning Co.) at 20±1° C. at beam intensities on the surface of the cured product of 365 nm=2.4 mW/cm$^2$ and 245 nm=24 μW/cm$^2$ for 120 seconds to develop color and to measure the photochromic properties ① to ③ and the optical property (refractive index) ④ described below.

① [Maximum absorption wavelength (λmax)]: A maximum absorption wavelength after the development of color was found by using a spectrophotometer MCPD 1000 manufactured by Otsuka Denshi Kogyo Co. The maximum absorption wavelength was related to the color tone at the time when the color was developed.

② [Color density {∈(120)−∈(0)}]: ∈(120)−∈(0) was found and was regarded to be a color density. Here, ∈ (120) is an absorbency of the photochromic compound at a maximum absorption wavelength of when it is irradiated with light for 120 seconds under the above-mentioned conditions to develop color, and ∈(0) is an absorbency at the same absorption wavelength as that of when a color is developed before being irradiated with light.

③ [Light resistance (%) of photochromic property]

The life until fatigued was measured by using a Xenon Fadometer FA-25AX-HC manufactured by Suga Shikenki Co., and was regarded to be the light resistance of photochromic property (also simply referred to as light resistance). The polymer was irradiated with light using the xenon fadometer for 200 hours, and the cured product was caused to develop color by the method described above. Namely, the life until fatigued is a ratio (%) of the light absorbency at a maximum absorption wavelength based on the color of the photochromic compound to the light absorbency with color developed before being irradiated with light of the fadometer.

④ [Refractive index]

The refractive index at 20° C. was measured by using Abbe's refractometer manufactured by Atago Co. Bromonaphthalene was used as the contact solution.

As a result, λmax was 610 nm, color density was 0.87, light resistance was 85% and refractive index was 1.58.

Examples 40 to 53

In the following Examples and Comparative Examples, polymerizable monomers (comonomers) and photochromic compounds represented by the following abbreviations were used for obtaining photochromic cured products.

[Comonomers]

TMPT: Trimethylolpropane trimethacrylate

3EGA: Triethylene glycol diacrylate

9EGA: Polyethylene glycol diacrylate having an average molecular weight of 532

MePEG: Methyletherpolyethylene glycol having an average molecular weight of 1000

ALMePEG (550): Methoxypolyethylene glycol allylether having an average molecular weight of 550

ALBuPEPPG (1600): Butoxypolyethylene glycol polypropylene glycol allylether having an average molecular weight of 1600

GMA: Glycidyl methacrylate

3G: Triethylene glycol dimethacrylate

4G: Tetraethylene glycol dimethacrylate

BPEM: 2,2-Bis(4-methacryloyloxy-polyethoxyphenyl) propane (ethylene oxide chain having an average value of 2.6)

BzMA: Benzyl methacrylate

MS: α-Methylstyrene

MSD: αa-Methylstyrene dimer

DVB: Divinyl benzene

[Photochromic compounds]

Chromene 1

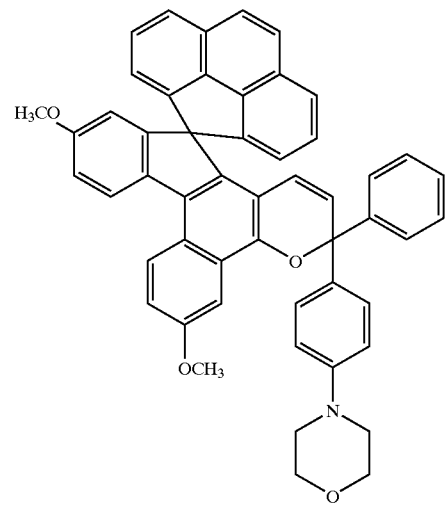

Chromene 2

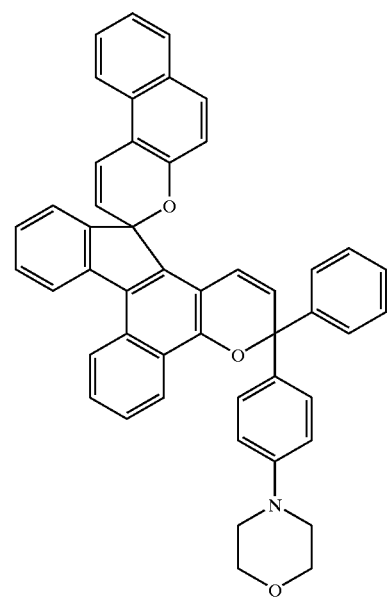

Chromene 3

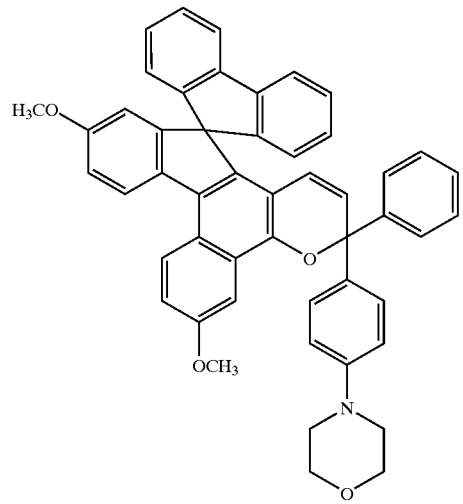

Chromene 4

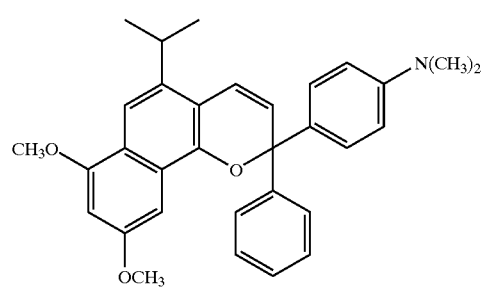

Chromene 5

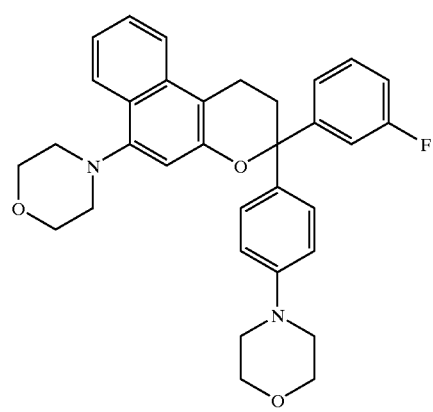

Chromene 6

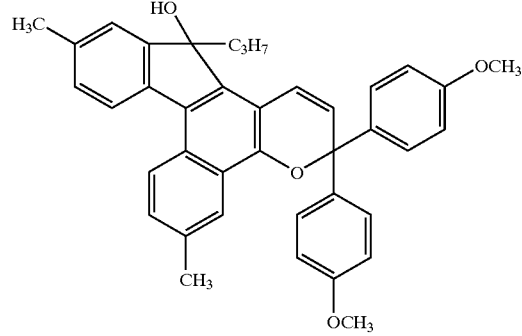

Chromene 7

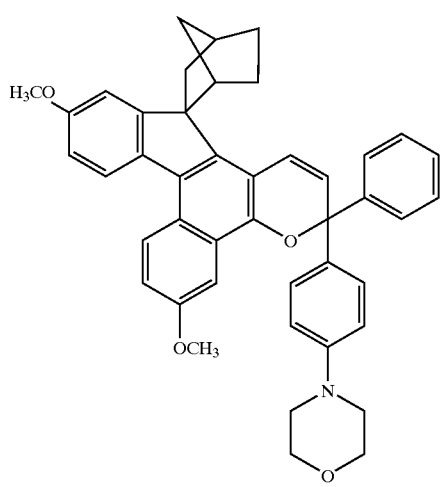

In Examples 40 to 53, cured products were obtained in the same manner as in Example 39 but changing the compositions of the photochromic polymerization-curable composition as shown in Tables 11 and 12, and their physical properties were measured. The results were as shown in Tables 11 and 12. In Tables 11 and 12, the column of "Component A" shows only the Example number of the polymerizable sulfur-containing compound that was used. It will be learned from Tables 11 and 12 that the photochromic cured products of the invention of Examples 39 to 53 exhibit refractive indexes of as high as 1.58 or more and light resistances of as large as about 80% or more.

Comparative Examples 4 to 7

By using the polymerizable sulfur-containing compounds containing much disulfide compound synthesized in Examples 35 to 38 as the component A, the photochromic polymerization-curable compositions shown in Table 12 were prepared to obtain cured products in the same manner as in Example 39 and to measure their physical properties. The results were as shown in Table 12.

As shown in Table 12, the photochromic cured products of Comparative Examples 4 to 7 have high refractive indexes but low light resistances.

TABLE 11

| Example | Component A (mass %) | Component B (mass %) | Component C* (mass %) | λmax (nm) | Color density | Light resistance (%) | Refractive index |
|---|---|---|---|---|---|---|---|
| 39 | 22 (78) | TMPT/ALMePEG(550)/3EGA/GMA/MS/MSD/DVB (4/2/1/4/6/3/2) | chromene 1 (0.03) | 610 | 0.87 | 83 | 1.58 |
| 40 | 22 (78) | TMPT/ALMePEG(550)/GMA/MS/MSD/DVB (4/2/5/6/3/2) | chromene 1 (0.03) | 610 | 0.85 | 80 | 1.58 |
| 41 | 23 (80) | TMPT/3EGA/GMA/MS/MSD (5/3/4/6/2) | chromene 5 (0.03) | 474 | 0.90 | 80 | 1.58 |
| 42 | 23 (80) | TMPT/9EGA/GMA/MS/MSD (4/4/6/4/2) | chromene 1 (0.03) | 610 | 0.86 | 78 | 1.58 |
| 43 | 24 (75) | TMPT/ALMePEG(550)/3G/MS/MSD (5/3/5/10/2) | chromene 2 (0.03) | 580 | 0.82 | 85 | 1.60 |
| 44 | 25 (80) | TMPT/ALBuPEPPG(1600)/MS/MSD (4/6/8/2) | chromene 1 (0.03) | 610 | 0.74 | 90 | 1.60 |
| 45 | 26 (77) | MePEG/4G/MSD/DVB (5/5/3/10) | chromene 1 (0.03) | 610 | 0.87 | 88 | 1.61 |
| 46 | 27 (75) | BzMA/9EGA/GMA/MS/MSD (10/3/6/4/2) | chromene 3 (0.03) | 600 | 0.79 | 83 | 1.62 |
| 47 | 28 (70) | TMPT/MS/MSD (15/13/2) | chromene 4 (0.03) | 588 | 0.83 | 87 | 1.61 |
| 48 | 29 (70) | BPEM/ALMePEG(550)/MS/MSD (10/3/15/2) | chromene 4 (0.03) | 588 | 0.80 | 81 | 1.61 |
| 49 | 30 (75) | TMPT/ALMePEG(550)/GMA/MS/MSD (5/3/8/7/2) | chromene 5 (0.03) | 474 | 0.91 | 85 | 1.59 |
| 50 | 31 (75) | TMPT/ALMePEG(550)/GMA/MS/MSD (5/3/8/7/2) | chromene 6 (0.03) | 576 | 0.83 | 84 | 1.60 |

Mark * represents parts by weight per 100 parts by weight of the whole polymerizable monomers.

TABLE 12

| Example | Component A (mass %) | Component B (mass %) | Component C* (mass %) | λmax (nm) | Color density | Light resistance (%) | Refractive index |
|---|---|---|---|---|---|---|---|
| 51 | 32 (76) | DVB/ALMePEG(550)/GMA/MS/MSD (5/3/8/6/2) | chromene 7 (0.03) | 570 | 0.81 | 87 | 1.59 |
| 52 | 33 (75) | TMPT/ALMePEG(550)/3G/MS/MSD (5/3/8/7/2) | chromene 1 (0.03) | 610 | 0.87 | 84 | 1.60 |
| 53 | 34 (75) | TMPT/3EGA/4G/MS/MSD (5/3/5/10/2) | chromene 1/chromene 5 (0.03/0.02) | 484 600 | 0.81 0.80 | 85 82 | 1.60 |

TABLE 12-continued

| Example | Component A (mass %) | Component B (mass %) | Component C* (mass %) | Amax (nm) | Color density | Light resistance (%) | Refractive index |
|---|---|---|---|---|---|---|---|
| Comp. Ex, 4 | 35 (78) | TMPT/ALMePEG(550)/3EGA/GMA/MS/MSD/DVB (4/2/1/4/6/3/2) | chromene 1 (0.03) | 610 | 0.88 | 70 | 1.58 |
| Comp. Ex. 5 | 36 (80) | TMPT/3EGA/GMA/MS/MSD (5/3/4/6/2) | chromene 5 (0.03) | 474 | 0.93 | 43 | 1.58 |
| Comp. Ex. 6 | 37 (80) | TMPT/ALBuPEPPG(1600)/MS/MSD (4/6/8/2) | chromene 1 (0.03) | 610 | 0.81 | 62 | 1.60 |
| Comp. Ex. 7 | 38 (75) | TMPT/ALMePEG(550)/GMA/MS/MSD (5/3/8/7/2) | chromene 5 (0.03) | 474 | 0.92 | 40 | 1.59 |

Mark * represents parts by weight per 100 parts by weight of the whole polymerizable monomers.

Effects of the Invention

According to the preparation method of the present invention, it is allowed to obtain in high yields the sulfur-containing compound that is highly pure, is little colored and has a thio group in the molecules without using the metal sodium that must be carefully handled. In using the sulfur-containing compound as an optical material or as a medical or agricultural starting material, therefore, the step of refining can be simplified, and the loss (drop of yield) can be decreased in the step of refining.

In particular, when the method of the present invention is put into practice in an atmosphere without substantially containing oxygen, it is allowed to greatly decrease the formation of by-product, i.e., disulfide compound which has chemical and physical properties resembling those of the sulfur-containing compound and is difficult to remove. When the present invention is put into practice relying upon the above method, therefore, a highly pure sulfur-containing compound is obtained containing smaller than 2 mol % of the disulfide compound which is the impurity that is contained in large amounts in the conventional sulfur-containing compound obtained by reacting the thiol compound with the compound capable of reacting with the mercapto group.

When the highly pure sulfur-containing compound is used in combination with the photochromic compound as a monomer for photochromic plastic lenses, very useful lenses are obtained exhibiting high refractive indexes and greatly improved light resistance of photochromic properties.

What is claimed is:

1. A photochromic polymerization-curable composition comprising:
   (a) a sulfur-containing compound having a thio group and at least one polymerizable functional group in the molecules thereof wherein the content of the compound having a disulfide bond by-produced during the synthesis of said sulfur-containing compound is suppressed to be not larger than 0.02 mols per mole of said sulfur-containing compound; and
   (b) a chromene compound;.

2. The photochromic cured product obtained by curing the photochromic polymerization-curable composition of claim 1 by polymerization.

3. The photochromic polymerization-curable composition according to claim 1, wherein said sulfur-containing compound (a) is obtained through the step of reacting a thiol compound (a-1) with an organic compound (a-2) having at least a functional group capable of forming a thio group by the reaction with a mercapto group and at least a polymerizable functional group in the molecules thereof.

4. The photochromic polymerization-curable composition according to claim 1, further containing (c) another polymerizable monomer copolymerizable with said sulfur-containing compound (a).

5. The photochromic polymerization-curable composition according to claim 1, wherein said sulfur-containing compound (a) is represented by any one of the general formulas (7) to (11), said general formula (7) represented as,

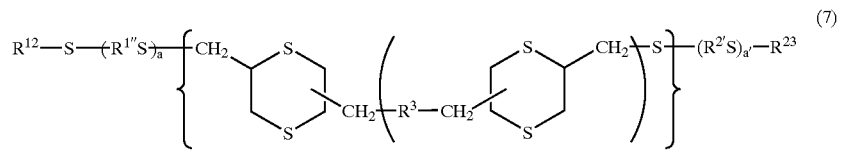

(7)

wherein
R$^{1'}$ and R$^{2'}$ are, independently from each other, alkylene groups with 1 to 4 carbon atoms that may have a substituent (without, however, including the number of carbon atoms of the substituent) or arylene groups with 6 to 12 carbon atoms that may have a substituent (without, however, including the number of carbon atoms of the substituent), the substituent of each of said alkylene group and of said arylene group being at least the one selected from the group consisting of an alkyl group, an aryl group, an aralkyl group, an alkoxy group, an alkylthio group, an aromatic heterocyclic group, a halogen atom excluding fluorine, and a group represented by the following formula (15)

(15)

wherein
R$^4$ is an alkylene group with 1 to 4 carbon atoms that may have a substituent (without, however, including the number of carbon atoms of the substituent), the substituent of said alkylene group being at least one group selected from the group consisting of an alkyl group, an aryl group, an aralkyl group, an alkoxy group, an alkylthio group, an aromatic heterocyclic group and a halogen atom excluding fluorine, $R^{14}$ is an alkyl group with 1 to 4 carbon atoms that may have a substituent (without, however, including the number of carbon atoms of the substituent), or a (meth)acryloyl group, the substituent of said alkyl group being at least the one selected from the group consisting of a polymerizable functional group, an aryl group, an aralkyl group, an alkoxy group, an alkylthio group, an aromatic heterocyclic group and a halogen atom excluding fluorine;

d is an integer of from 0 to 10, and d' is an integer of 0 or 1;

$R^{12}$ and $R^{13}$ are, independently from each other, an alkyl group with 1 to 4 carbon atoms that may have a substituent (without, however, including the number of carbon atoms of the substituent), or a (meth)acryloyl group, the substituent of said alkyl group being at least the one selected from the group consisting of a polymerizable functional group, an aryl group, an aralkyl group, an alkoxy group, an alkylthio group, an aromatic heterocyclic group and a halogen atom excluding fluorine;

$R^3$ is a divalent group represented by the following formula (13),

(13)

wherein $R^5$ is an alkylene group with 1 to 4 carbon atoms that may have a substituent (without, however, including the number of carbon atoms of the substituent), an arylene group with 6 to 12 carbon atoms that may have a substituent (without, however, including the number of carbon atoms of the substituent), a divalent aromatic heterocyclic group that may have a substituent, or a divalent group represented by the following formula (14),

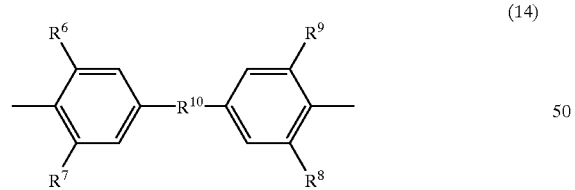

(14)

wherein $R^6$, $R^7$, $R^8$ and $R^9$ are, independently from each other, halogen atoms excluding fluorine atoms, orhydrogen atoms, and $R^{10}$ is an alkylene group having 1 to 3 carbon atoms or sulfur atoms), the substituent of each of said alkylene group, arylene group and divalent aromatic heterocyclic group being the same as the substituent of the alkylene group with 1 to 4 carbon atoms that may have a substituent in the above formula (12), and e being an integer of 0 to 5; and a and a' are, independently from each other, integers of 0 to 10, c is an integer of from 0 to 6, c' is 0 or 1 and, when c' is 0, the sum of a and a' is not smaller than 2;

said general formula (8) represented as,

(8)

wherein $R^{15}$ is a monovalent to trivalent aromatic group with 6 to 14 carbon atoms which may have a substituent (without, however, including the number of carbon atoms of the substituent) or a monovalent to trivalent aromatic heterocyclic group with 3 to 12 carbon atoms which may have a substituent (without, however, including the number of carbon atoms of the substituent), the substituent of each of these aromatic group and aromatic heterocyclic group being the same as the substituent of the alkylene group, f is an integer of 0 or 1, f' is an integer of 1 to 3, $R^{11}$ is an alkyl group with 1 to 4 carbon atoms that may have a substituent (without, however, including the number of carbon atoms of the substituent), or a (meth)acryloyl group, the substituent of said alkyl group being at least the one selected from the group consisting of a polymerizable functional group, an aryl group, an aralkyl group, an alkoxy group, an alkylthio group, an aromatic heterocyclic group and a halogen atom excluding fluorine;

said general formula (9) represented as,

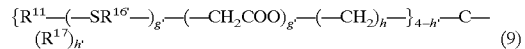

(9)

wherein $R^{16'}$ is an alkylene group with 1 to 4 carbon atoms that may have a substituent (without, however, including the number of carbon atoms of the substituent), the substituent of said alkylene group being the same as the substituent of the alkylene group with 1 to 4 carbon atoms which may have a substituent denoted by $R^{1'}$ and $R^{2'}$ in the above general formula (7), $R^{17}$ is a hydrogen atom or an alkyl group with 1 to 4 carbon atoms which may have a substituent (without, however, including the number of carbon atoms of the substituent), the substituent of said alkyl group being the same as the substituent other than the alkyl group in the alkylene group, g is an integer of 0 or 10, g' is an integer of 0 or 1, h is an integer of 0 to 5 and, when g' is 1, h is an integer of 1 to 5, and h' is 0 or 1;

$R^{11}$ is an alkyl group with 1 to 4 carbon atoms that may have a substituent (without, however, including the number of carbon atoms of the substituent), or a (meth)acryloyl group, the substituent of said alkyl group being at least the one selected from the group consisting of a polymerizable functional group, an aryl group, an aralkyl group, an alkoxy group, an alkylthio group, an aromatic heterocyclic group and a halogen atom excluding fluorine;

said general formula (10) represented as,

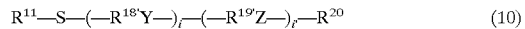

(10)

wherein $R^{18'}$ and $R^{19'}$ are, independently from each other, alkylene groups with 1 to 4 carbon atoms which may have a substituent (without, however, including the number of carbon atoms of the substituent), or arylene groups with 6 to 12 carbon atoms which may have a substituent (without, however, including the number of carbon atoms of the substituent), the substituent of each of said alkylene group and said arylene group being the same as the substituent of the alkylene group with 1 to 4 carbon atoms which may have a substituent or of the arylene group with 6 to 12 carbon atoms which may have a substituent denoted by $R^{1'}$ and $R^{2'}$ in the above general formula (7), and $R^{20}$ is an alkyl group with 1 to 4 carbon atoms which may have substituent (without, however, including the number of carbon atoms of the substituent), an aryl group with 6 to 12 carbon atoms which may have a substituent (without, however, including the number of carbon atoms of the substituent), or an aralkyl group which may have a substituent, the substituent of said alkyl group being the same as the substituent other than the alkyl group in the alkylene group, Y is an oxygen atom or a sulfur atom, Z are simultaneously oxygen atoms, i and i' are, independently from each other, integers of 0 to 10, and the sum of i and i' are not smaller than 1, $R^{11}$ is an alkyl group with 1 to 4 carbon atoms that may have a substituent (without, however, including the number of carbon atoms of the substituent), or a (meth)acryloyl group, the substituent of said alkyl group being at least the one selected from the group consisting of a polymerizable functional group, an aryl group, an aralkyl group, an alkoxy group, an alkylthio group, an aromatic heterocyclic group and a halogen atom excluding fluorine;

a compound represented by the following general formula (11),

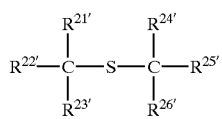

(11)

wherein $R^{21'}$, $R^{22'}$, $R^{23'}$, $R^{24'}$, $R^{25'}$ and $R^{26'}$ are, independently from each other, hydrogen atoms or groups represented by the following formula (17),

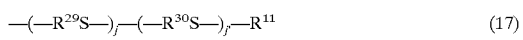

(17)

wherein $R^{29}$ and $R^{30}$ are, independently from each other, alkylene groups with 1 to 4 carbon atoms that may have a substituent (without, however, including the number of carbon atoms of the substituent), the substituent of said alkylene group being the same as the substituent in the alkylene group with 1 to 4 carbon atoms which may have a substituent denoted by $R^{1'}$ and $R^{2'}$ in the above general formula (7), j and j' are, independently from each other, integers of 0 to 4, and the sum of j and j' is not smaller than 1, $R^{11}$ is an alkyl group with 1 to 4 carbon atoms that may have a substituent (without, however, including the number of carbon atoms of the substituent), or a (meth)acryloyl group, the substituent of said alkyl group being at least the one selected from the group consisting of a polymerizable functional group, an aryl group, an aralkyl group, an alkoxy group, an alkylthio group, an aromatic heterocyclic group and a halogen atom excluding fluorine;

at least one of $R^{21'}$, $R^{22'}$, $R^{23'}$, $R^{24'}$, $R^{25'}$ and $R^{26'}$ is a group represented by the general formula (5)

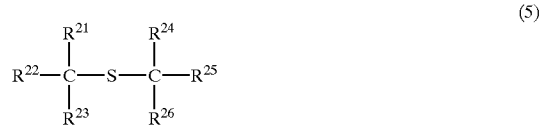

(5)

wherein $R^{21}$, $R^{22}$, $R^{23}$, $R^{24}$, $R^{25}$ and $R^{26}$ are, independently from each other, hydrogen atoms or groups represented by the following formula (16),

(16)

wherein $R^{27}$ and $R^{28}$ are, independently from each other, alkylene groups with 1 to 4 carbon atoms that may have a substituent (without, however, including the number of carbon atoms of the substituent), the substituent of said alkylene group being the same as the substituent of the alkylene group with 1 to 4 carbon atoms which may have a substituent represented by $R^1$ and $R^2$ in the above general formula (1), j and j' are, independently from each other, integers of 0 to 4, and the sum of j and j' is not smaller than 1; and at least one of $R^{21}$, $R^{22}$, $R^{23}$, $R^{24}$, $R^{25}$ and $R^{26}$ is the group represented by the above formula (16).

6. A photochromic polymerization-curable composition according to claim 1, wherein said chromene compound (b) is represented by any one of the general formulas (18) to (25), said general formula (18) represented as,

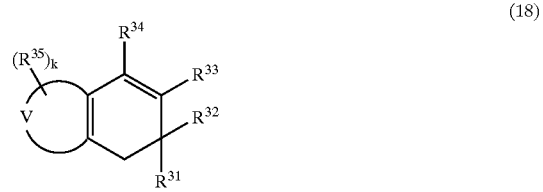

(18)

wherein a group represented by the following formula (26),

(26)

is a substituted, or unsubstituted aromatic hydrocarbon group or a substituted or unsubstituted unsaturated heterocyclic group, $R^{33}$, $R^{34}$ and $R^{35}$ are alkyl groups, alkoxy groups, aralkoxy groups, amino groups, substituted amino groups, cyano groups, substituted or unsubstituted aryl groups, halogen atoms, aralkyl groups, hydroxy groups, substituted or unsubstituted alkynyl groups, substituted or unsubstituted heterocyclic groups having a nitrogen atom as a hetero atom and in which the nitrogen atom and a pyran ring or a ring of the group represented by the above general formula (18) are bonded together, or condensed heterocyclic groups in which the heterocyclic group is condensed with an aromatic hydrocarbon ring or with an aromatic heterocyclic ring, k is an integer of 0 to 6, $R^{31}$ and $R^{32}$ are, independently from each other, groups represented by the following formula (27),

(27)

wherein $R^{36}$ is a substituted or unsubstituted aryl group or a substituted or unsubstituted heteroaryl group, $R^{37}$ is a hydrogen atom, an alkyl group or a halogen atom, m is an integer of 1 to 3, groups represented by the following formula (28),

(28)

wherein $R^{38}$ is a substituted or unsubstituted aryl group, or a substituted or unsubstituted heteroaryl group, and m' is an integer of 1 to 3, substituted or unsubstituted aryl groups, substituted or unsubstituted heteroaryl groups or alkyl groups, or $R^{31}$ and $R^{32}$ together may constitute an aliphatic hydrocarbon ring or an aromatic hydrocarbon ring, wherein the substituents in the substituted aryl groups or in the substituted heteroaryl groups in the above formulas (27) and (28) or denoted by $R^{31}$ and $R^{32}$ are the same as those denoted by $R^{33}$ to $R^{35}$;

said general formula (19) represented as,

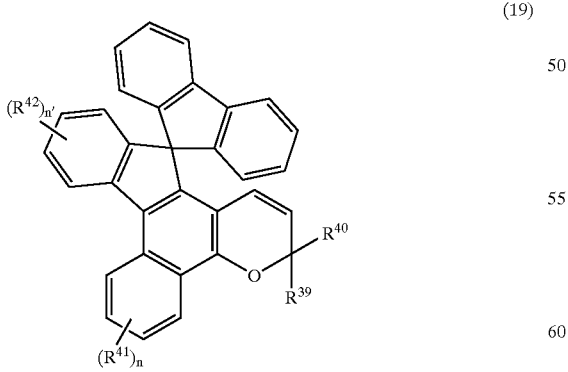

(19)

wherein $R^{39}$ and $R^{40}$ are, independently from each other, the same as those denoted by $R^{31}$ and $R^{32}$ in the above general formula (18), $R^{41}$ and $R^{42}$ are the same as those denoted by $R^{33}$, $R^{34}$ and $R^{35}$ in the above general formula (18), and n and n' are, independently from each other, integers of 0 to 4;

said general formula (20) represented as,

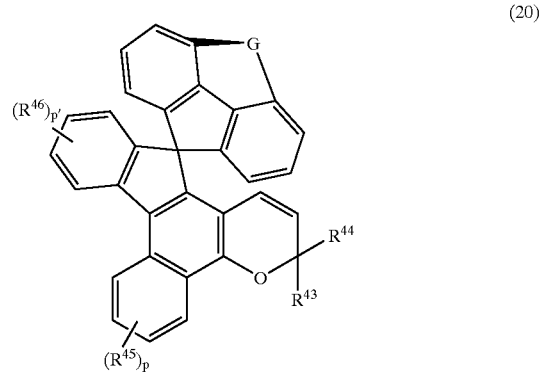

(20)

wherein $R^{43}$ and $R^{44}$ are, independently from each other, the same as those denoted by $R^{31}$ and $R^{32}$ in the above general formula (18), $R^{45}$ and $R^{46}$ are the same as those denoted by $R^{33}$, $R^{34}$ and $R^{35}$ in the above general formula (18), p and p' are, independently from each other, integers of 0 to 4, and G is any one of the group represented by the following general formulas,

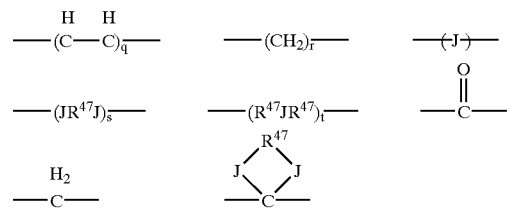

wherein J is an oxygen atom or a sulfur atom, $R^{47}$ is an alkylene group with 1 to 6 carbon atoms, and q, r, s and t are, independently from each other, integers of 1 to 4;

said general formula (21) represented as,

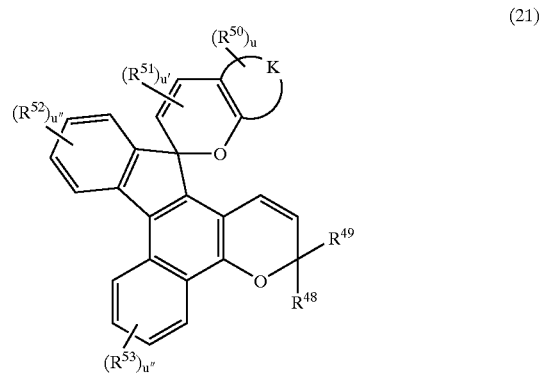

(21)

wherein $R^{48}$ and $R^{49}$ are, independently from each other, the same as those denoted by $R^{31}$ and $R^{32}$ in the above general formulas (8), $R^{50}$, $R^{51}$, $R^{52}$ and $R^{53}$ are the same as those denoted by $R^{33}$, $R^{34}$ and $R^{35}$ in the above general formula (18), u is an integer of 0 to 6, u', u" and u'" are, independently from each other, integers of 0 to 4, and the following formula (29),

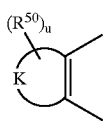
(29)

represents a substituted or unsubstituted aromatic hydrocarbon group, or a substituted or unsubstituted unsaturated heterocyclic group;

said general formula (22) represented as,

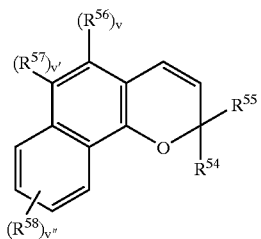
(22)

wherein $R^{54}$ and $R^{55}$ are, independently from each other, the same as those denoted by $R^{31}$ and $R^{32}$ in the general formula (18), $R^{56}$, $R^{57}$ and $R^{58}$ are the same as those denoted by $R^{33}$, $R^{34}$ and $R^{35}$ in the above general formula (18), v' and v" are, independently from each other, integers of 0 or 1, v''' is an integer of 0 to 4;

said general formula (23) represented as,

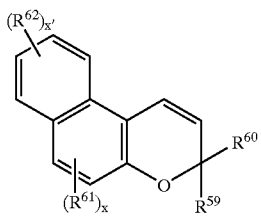
(23)

wherein $R^{59}$ and $R^{60}$ are, independently from each other, the same as those denoted by $R^{31}$ and $R^{32}$ in the above general formula (18), $R^{61}$ and $R^{62}$ are the same as those denoted by $R^{33}$, $R^{34}$ and $R^{35}$ in the above general formula (18), x is an integer of 0 to 2, and x' is an integer of 0 to 4;

said general formula (24) represented as,

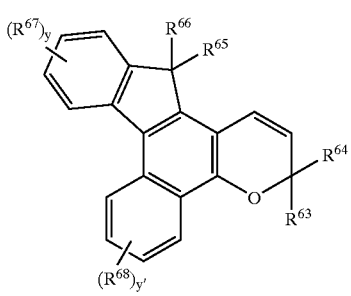
(24)

wherein $R^{63}$ and $R^{64}$ are, independently from each other, the same as those denoted by $R^{31}$ and $R^{32}$ in the above general formula (18), $R^{65}$, $R^{66}$, $R^{67}$ and $R^{68}$ are the same as those denoted by $R^{33}$, $R^{34}$ and $R^{35}$ in the above general formula (18), and y and y' are, independently from each other, integers of 0 to 4;

said general formula (25) represented as,

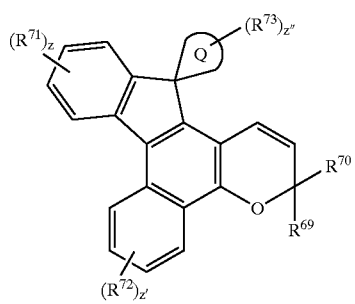
(25)

wherein $R^{69}$ and $R^{70}$ are, independently from each other, the same as those denoted by $R^{31}$ and $R^{32}$ in the above general formula (18), $R^{71}$, $R^{72}$ and $R^{73}$ are the same as those denoted by $R^{33}$, $R^{34}$ and $R^{35}$ in the above general formula (18), and z and z' are, independently from each other, integers of 0 to 4, z''' is an integer of 0 to 6, and the following formula (30)

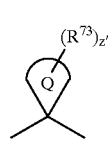
(30)

represent an aliphatic hydrocarbon ring that may have up to 6 substituents.

7. A photochromic polymerization-curable composition of claim 3, wherein said thiol compound (a-1) and said organic compound (a-2) are reacted together under the conditions expressed by the following formula, $$A \leq S \times M \times 7.5$$

wherein A is a mol number of water contained in the reaction system, S is a mol number of the thiol compound, and M is an number of mercapto groups present in one molecule of said thiol compound, in an atmosphere without substantially containing oxygen.

* * * * *